US006884871B2

(12) United States Patent
Luyten et al.

(10) Patent No.: US 6,884,871 B2
(45) Date of Patent: Apr. 26, 2005

(54) ISOLATION AND USE OF TISSUE GROWTH-INDUCING FRZB PROTEIN

(75) Inventors: Frank P. Luyten, Rockville, MD (US); Malcolm Moos, Jr., Bethesda, MD (US); Bang Hoang, University Heights, OH (US); Shouwen Wang, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 409 days.

(21) Appl. No.: 10/014,055

(22) Filed: Dec. 7, 2001

(65) Prior Publication Data

US 2003/0139591 A1 Jul. 24, 2003

Related U.S. Application Data

(63) Continuation of application No. 08/729,452, filed on Oct. 11, 1996, now abandoned.

(51) Int. Cl.⁷ ...................... C07K 14/475; C07H 21/04; C12P 21/02

(52) U.S. Cl. ...................... 530/350; 536/23.5; 435/69.1

(58) Field of Search ........................ 530/350; 536/23.5; 435/69.1

(56) References Cited

U.S. PATENT DOCUMENTS

| | | |
|---|---|---|
| 5,578,569 A | 11/1996 | Tam |
| 6,133,232 A | 10/2000 | De Robertis et al. |

FOREIGN PATENT DOCUMENTS

| | | |
|---|---|---|
| WO | WO 96 14335 | 5/1996 |
| WO | WO 97 48275 A | 12/1997 |

OTHER PUBLICATIONS

Adler, P.N., et al. (1990) Molecular Structure of frizzled, a Drosophila Tissue Polarity Gene. *Genetics* 126:401–416.
Aebersold, R. H., et al. (1987) Internal amino acid sequence analysis of proteins separated by one– or two–dimensional gel electrophoresis after in situ protease digestion on nitrocellulose. *Proc. Natl. Acad. Sci. USA* 84:6970–6974.
Bhanot, P., et al. (1996) A new member of the frizzled family from Drosophila functions as a Wingless receptor. *Nature* 382:225–230.
Bouwmeester T., et al. (1996) Cerberus is a head–inducing secreted factor expressed in the anterior endoderm of Spemann's organizer, *Nature* 382:595–601.
Bowie, J. U., et al. (1990) Deciphering the Message in Protein Sequences: Tolerance to Amino Acid Substitutions. *Science* 247:1306–1310.

Camac, G., et al. (1996) The homeobox gene Siemois is a target of the Wnt dorsalisation pathway and triggers organiser activity in the absence of mesoderm. *Development* 122:3055–3065.
Chan, S. D. H., et al. (1992) Two Homologs of the Drosophila Polarity Gene frizzled (fz) Are Widely Expressed in Mammalian Tissues. *J. Biol Chem.* 267(35):25202–25207.
Chang, J. T., et al. (1999) Cloning and characterization of a secreted frizzled–related protein that is expressed by the retinal pigment epithelium . *Human Mol. Genetics* 8(4):575–583.
Chang, S.C., et al. (1994) Cartilage–derived Morphogenetic Proteins. *J. Biol. Chem.* 269(45):28227–28234.
Christian, J. L., et al. (1993) Interactions between Xwnt–8 and Spermann organizer signaling pathways generate dorsoventral pattern in the embryonic mesoderm of Xenopus. *Genes & Development* 7:13–28.
Cui, Y., et al. (1995) Xwnt–8b: a maternally expressed *Xenopus Wnt* gene with a potential role in establishing the dorsoventral axis. *Development* 121:2177–2186.
De Robertis, E. M., et al. (1996) A common plan for dorsoventral patterning in Bilateria. *Nature* 380:37–40.
Epifano, O., et al. (1995) Coordinate expression of the three zona pellucida genes during mouse cogenesis. *Development* 121:1947–1956.
Erlebacher, A., et al. (1995) Toward a Molecular Understanding of Skeletal Development *Cell* 80:371–378.
Finch, P. W., et al. (1997) Purification and moelcular cloning of a secreted. Frizzled–related antagonist of Wnt action. *Proc. Natl Acad Sci. USA* 94:6770–6775.
Harland, R. M. (1991) In Situ Hybridization: An Improved Whole–Mount Method for Xenopus Embryos. *Meth. Cell Biol.* 36:685–695.
Hoang, B., et al. (1996) Primary Structure and Tissue Distribution of FRZB, a Novel Protein Related to Drosophila Frizzled, Suggest a Role in Skeletal Morphogenesis. *J. Biol. Chem.* 271(42):26131–26137.
Hoppler S., et al. (1996) Expression of a dominant–negative Wnt blocks Induction of MyoD in Xenopus embryos. *Genes & Development* 10:2805–2817.
Kao, K. R., et al. (1988) The Entire Mesodermal Mantle Behaves as Spemann's Organizer in Dorsoanterior Enhanced *Xenopus laevis* Embryos. *Develop. Biol.* 127:64–77.
Kay, B. K. (1991) Injection of Oocytes and Embryos. *Methods Cell Biol.* 36:663–669.
Lemaire, P., et al. (1995) Expression Cloning of Siarnois a Xenopus Homeobox Gene Expressed in Dorsal–Vegetal Cells of Blastulae and Able to Induce a Complete Secondary Axis. *Cell* 81:85–94.

(Continued)

*Primary Examiner*—David Romeo
(74) *Attorney, Agent, or Firm*—Knobbe, Martens, Olson & Bear LLP

(57) ABSTRACT

An isolated cDNA encoding a growth-inducing protein, Frzb, capable of stimulating bone, cartilage, muscle and nerve tissue formation. The CDNA and protein sequences of human and bovine frzb are provided. Production and purification of recombinant Frzb are also described.

10 Claims, 4 Drawing Sheets

OTHER PUBLICATIONS

Leyns, L., et al. (1997) Frzb–1 Is a Secreted Antagonist of Wnt Signaling Expressed in the Spemann Organizer. *Cell* 88:747–756.

Luyten, F. P., et al. (1988) Insulin–like Growth Factors Maintain Steady–State Metabolism of Proteoglycans in Bovine Articular Cartilage Explants. *Archives of Biochem. and Biophys.* 267(2):416–425.

Luyten, F. P., et al. (1989) Purification and Partial Amino Acid Sequence of Osteogenin, a Protein Initiating Bone Differentiation. *J. Biol. Chem.* 264(23):13377–13380.

Luyten, F. P., et al. (1994) Recombinant Bone Morphogenetic Protein–4, Transforming Growth Factor–$\beta_1$, and Activin A Enhance the Cartilage Phenotype of Articular Chondrocytes in Vitro. *Exper. Cell Res.* 210:224–229.

Marieb, E. N. (1992) In, Human Anatomy and Physiology, The Benjamin/Cummings Publ. Co., $2^{nd}$ Ed., 373–375.

Mayr, T., et al. (1997) Fritz: a secreted frizzled–related protein that inhibits Wnt activity. *Mech. Develop.* 63:09–125.

Melkonyan, H.S., et al. (1997) SARPs: a family of secreted apoptosis–related proteins. *Proc. Natl. Acad. Sci. USA* 94:13636–13641.

Moon, R. T. (1993) In Pursuit of the Functions of the Wnt Family of Developmental Regulators: Insights from *Xenopus laevis*, BioEssays 15(2):91–97.

Moos, M., Jr., et al. (1995) Anti–Dorsalizing Morphogenetic Protein is a novel TGF–$\beta$ homolog expressed in the Spemann organizer. *Development* 121:4293–4301.

Moos. M., Jr., et al. (1988) Reproducible High Yield Sequencing of Proteins Electrophoretically Separated and Transferred to an Inert Support. *J. Biol. Chem.* 263(13):6005–6008.

Muthukumaran, N., et al. (1985) Comparison of Bone Inductive Proteins of Rat and Porcine Bone Matrix. *Biochem. Biophys. Res. Comm.* 131(1):37–41.

Nardi, J. B., et al. (1976) Polarity and gradients in lepidopteran wing epidermis. *J. Embryol. exp. Morph.* 36(3):489–512.

Nathan, C. and Sporn, M. (1991) Cytokines in Context. *J. Cell Biol.* 113(5):981–986.

Nusse, R. and Varmus, H. E. (1992) Wnt. Genes. *Cell* 69:1073–1087.

Paralkar, V. M., et al. (1989) Affinity of Osteogenin, an Extracellular Bone Matrix Associated Protein Initiating Bone Differentiation, for Concanavalin A. *Biochem. Biophys. Res. Comm.* 160(2):419–424.

Parr, B. A. and McMahon, A. P. (1994) Wnt genes and vertebrate development. *Cur. Opin. Genet. Develop.* 4:523–528.

Pelton, R. W., et al. (1989) Expression of transforming growth factor $\beta 2$ RNA during murine embryogenesis. *Development* 106:759–767.

Rattner, A., et al. (1997) A family of secreted proteins contains homology to the cysteine–rich ligand–binding domain of frizzled receptors. *Proc. Nat'l. Acad. Sci. USA* 94:2859–2863.

Richter, K., et al. (1988) Gene expression in the embryonic nervous system of *Xenopus laevis*. *Proc. Natl. Acad. Sci. USA* 85:8086–8090.

Sambrook, J., et al. (Nov. 1989) Molecular Cloning: A Laboratory Manual Second Edition vols. 1, 2 and 3. Cold Spring Harbor Laboratory Press: Cold Spring Harbor, New York USA pp. 16.2, 17.2.

Sato, S. M. and Sargent, T. D. (1991) Localized and inducible expression of *Xenopus–posterios* (*Xpo*), a novel gene active in early frog embryos, encoding a protein with a 'CCHC' finger domain. *Development* 112:747–753.

Scales, J. B., et al. (1990) Two Distinct Xenopus Genes with Homology to MyoD1 Are Expressed before Somite Formation in Early Embryogenesis. *Mol. Cell. Biol.* 10(4):1516–1524.

Shirozu, M., et al. (1996) Characterization of Novel Secreted and Membrane Proteins Isolated by the Signal Sequence Trap Method. *Genomics* 37:273–280.

Slack, J. M. W. (1994) Inducing factors in Xenopus early embryos. *Cur. Biol.* 4(2):116–126.

Smith, W. C. and Harland, R. M. (1991) Injected Xwnt–8 RNA Acts Early in Xenopus Embryos to Promote Formation of a Vegetal Dorsalizing Center. *Cell* 67:753–765.

Smith, W. C., et al. (1995) A Nodal–Related Gene Defines a Physical and Functional Domain within the Spemann Organizer. *Cell* 82:37–46.

Sokol, S., et al. (1991) Injected Wnt RNA Induces a Complete Body Axis in Xenopus Embryos. *Cell* 67:741–752.

Tempst, P., et al. (1990) Internal sequence analysis of proteins separated on polyacrylamide gels at the submicrogram level: Improved methods, applications and gene cloning strategies. *Electrophoresis* 11:537–553.

Tsukamoto, A. S., et al. (1988) Expression of the int–1 Gene in Transgenic Mice Is Associated with Mammary Gland Hyperplasia and Adenocarcinomas in Male and Female Mice. *Cell* 55:619–625.

van Leeuwen, F. and Nusse, R. (1995) Oncogene activation and oncogene cooperation in MMTV–induced mouse mammary cancer. *Cancer Biol.* 6:127–133.

Vinson, C. R. and Adler, P. N. (1987) Directional non–cell autonomy and the transmission of polarity information by the frizzled gene of Drosophila. *Nature* 329:549–551.

Vinson, C. R., et al. (1989) A Drosophila tissue polarity locus encodes a protein containing seven potential transmembrane domains. *Nature* 338:263–264.

Vukicevic, S., et al. (1994) Developing Human Lung and Kidney are Major Sites for Synthesis of Bone Morphogenetic Protein–3 (Osteogenin). *J. Histochem. Cytochem.* 42(7):869–875.

Wadsworth, W. G. and Hedgecock, E. M. (1996) Hierarchical guidance cues in the developing nervous system of C. elegans. *BioEssays* 18(5):355–362.

Wang, S., et al. (1995) DNA Sequencing from Single Phage Plaques Using Solid–Phase Magnetic Capture. *BioTechniques* 18(1):130–135.

Wang, S., et al. (1997) Frzb, a Secreted Protein Expressed in the Spemann Organizer, Binds and Inhibits Wnt–8. *Cell* 88:757–766.

Wang, Y., et al. (1996) A Large Family of Putative Transmembrane Receptors Homologous to the Product of the Drosophila Tissue Polarity Gene frizzled *J. Biol. Chem.*, 271(8):4468–4476.

Wolf, V., et al. (1997) DDC–4, an apoptosis–associated gene, is a secreted frizzled relative. *FEBS Letters* 471:385–389.

Yang–Snyder, J., et al. (1996) A frizzled homolog functions in a vertebrate Wnt signaling pathway. *Current Biology* 6(10):1302–1306.

Zhao, Z., et al. (1995) A Human Homologue of the Drosophila Polarity Gene frizzled Has Been Identified and Mapped to 17q21.1 *Gneomics* 27:370–373.

Zheng, L., et al. (1995) frizzled regulates mirror–symmetric pattern formation in the *Drosophila* eye. *Development* 121:3045–3055.

FIG. 1

```
bovine   MVCGSR GGML LLPAGLLALAL ALCLLRV PGA RAAACEPVRI PLCKSLPWNM   50
human    ------P---- --R-------- ---------- ---------- ----------   50 bovine   TKMPNHLHHS TQANAILAIE QFEGLLGTHC SPDLLFFLCA MYAPICTIDF      100
human    ---------- ---------- ---------- ---------- ----------    100 bovine   QHEPIKPCKS VCERARQGCE PILIKYRHSW PESLACEELP VYDRGVCISP      150
human    ---------- ---------- ---------- --N------- ----------    150 bovine   EAIVTADGAD FPMDSSNGNC RGASSERCKC KPVRATQKTY FRNNYNYVIR      200
human    ---------- ---------- ---------- --I------- ----------    200 bovine   AKVKEIKTKC HDVTAVVEVK EILKASLVNI PRETVNLYTS SGCLCPPLNV      250
human    ---------- ---------- ----S----- --D------- ----------    250 bovine   NEEYLIMGYE DEERSRLLLV EGSIAEKWKD RLGKKVKRWD MKLRHLGLNT      300
human    ----I----- ---------- ---------- ---------- -------SK      300 bovine   SDSSHSDSTQ SQKPGRNSNS RQARN                                 325
human    ----N----- ---S-----P -----                                 325
```

*FIG.2A*

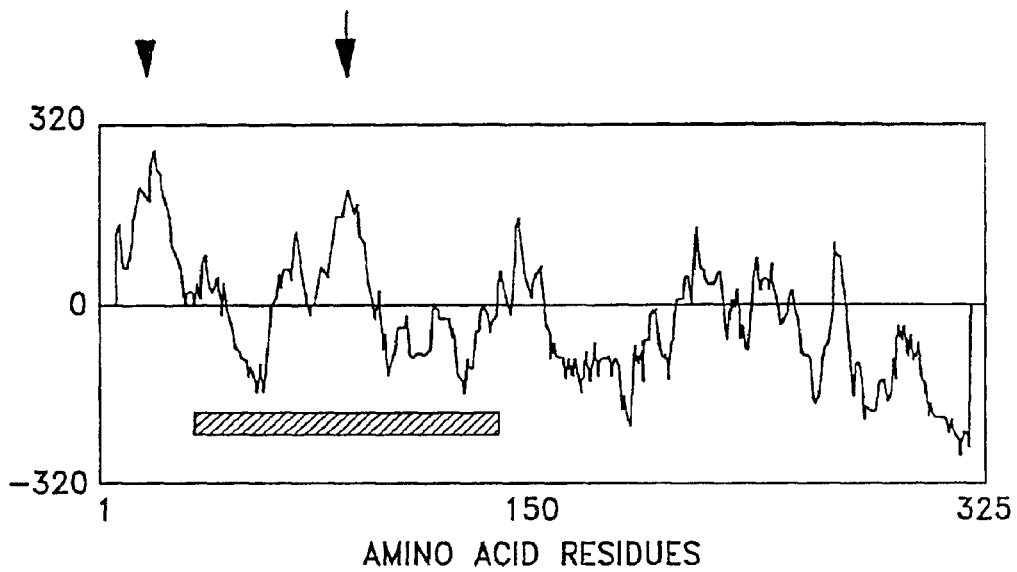

*FIG.2B*

| | | | | | | |
|---|---|---|---|---|---|---|
| Rat fz-1 | QQFISIELCT | DIAYNQTHMP | NLIGHTNQED | AGLEVHQFYP | LVKVQCSAEL | | 160 |
| Drosophila frizzled | CEPITISICK | NIPYNMHMP | NLIGHTKQEE | AGLEVHQEAP | LVKIGCSDDL | | 102 |
| bovine frzb | CEPVRIELCK | SLPWNMTKMP | NHLHSTQAN | ALLAIEQFEG | LLGTHCSPDL | | 84 |
| human frzb | CEPVRIELCK | SLPWNMTKMP | NHLHSTQAN | ALLAIEQFEG | LLGTHCSPDL | | 84 |

| | | | | | | |
|---|---|---|---|---|---|---|
| Rat fz-1 | KEFLCSMYAP | VCTIVLEQAIP | --PCRSICER | A-QCEALMN | KFGFQWPDTL | | 207 |
| Drosophila frizzled | QIFLCSLYVP | VCTILERPIP | --PCRSLCES | AR-VCEKLMK | TYNFNWPENL | | 149 |
| bovine frzb | LFFLCAMYAP | ICTIDFQHEP | IKPCKSVCER | AROCEPILI | KYRHSWPESL | | 134 |
| human frzb | LFFLCQMYAP | ICTIDFQHEP | IKPCKSVCER | AROCEPILI | KYRHSWPENL | | 134 |

| | | | | | | |
|---|---|---|---|---|---|---|
| Rat fz-1 | KCEKFPVHGR | GELC | | | | | 221 |
| Drosophila frizzled | ECSKFPVHGG | EDLC | | | | | 163 |
| bovine frzb | ACEELPVYDR | G-VC | | | | | 147 |
| human frzb | ACEELPVYDR | G-VC | | | | | 147 |

*FIG.3*

```
                                                                              *
    xFrzb    MSPTRKLDSF  L----LLVIP  GLVLLLLPNA  YCASCEPVRI  PMCKSMPWNM    46
    bFrzb    MVCGSRGGML  LLPAGLLALA  ALCLLRVPGA  RAAACEPVRI  PLCKSLPWNM    50
    hFRZB    MVCGSPGGML  LLRAGLLALA  ALCLLRVPGA  RAAACEPVRI  PLCKSLPWNM    50

Consensus    MVCGS.GGML  LL.AGLLALA  ALCLLRVPGA  RAAACEPVRI  PLCKSLPWNM    50 xFrzb    TKMPNHLHHS  TQANAILAIE  QFEGLITTEC  SQDLLFFLCA  MYAPICTIDF    96
    bFrzb    TKMPNHLHHS  TQANAILAIE  QFEGLLGTHC  SPDLLFFLCA  MYAPICTIDF   100
    hFRZB    TKMPNHLHHS  TQANAILAIE  QFEGLLGTHC  SPDLLFFLCA  MYAPICTIDF   100

Consensus    TKMPNHLHHS  TQANAILAIE  QFEGLLGTHC  SPDLLFFLCA  MYAPICTIDF   100 xFrzb    QHEPIKPCKS  VCERARAGCE  PILIKYRHTW  PESLACEELP  VYDRGVCISP   146
    bFrzb    QHEPIKPCKS  VCERARQGCE  PILIKYRHSW  PESLACEELP  VYDRGVCISP   150
    hFRZB    QHEPIKPCKS  VCERARQGCE  PILIKYRHSW  PENLACEELP  VYDRGVCISP   150

Consensus    QHEPIKPCKS  VCERARQGCE  PILIKYRHSW  PESLACEELP  VYDRGVCISP   150 xFrzb    AEIVTVEQGT  DSMPDFPMDS  NNGNCGSTAG  EHCKCKPMKA  SQKTYLKNNY   196
    bFrzb    EAIVTAD-G-  ---ADFPMDS  SNGNCRGASS  ERCKCKPVRA  TQKTYFRNNY   195
    hFRZB    EAIVTAD-G-  ---ADFPMDS  SNGNCRGASS  ERCKCKPIRA  TQKTYFRNNY   195

Consensus    EAIVTAD-G-  ---ADFPMDS  SNGNCRGASS  ERCKCKP.RA  TQKTYFRNNY   200 xFrzb    NYVIRAKVKE  VKVKCHDATA  IVEVKEILKS  SLVNIPKDTV  TLYTNSGCLC   246
    bFrzb    NYVIRAKVKE  IKTKCHDVTA  VVEVKEILKA  SLVNIPRETV  NLYTSSGCLC   245
    hFRZB    NYVIRAKVKE  IKTKCHDVTA  VVEVKEILKS  SLVNIPRDTV  NLYTSSGCLC   245

Consensus    NYVIRAKVKE  IKTKCHDVTA  VVEVKEILKS  SLVNIPRDTV  NLYTSSGCLC   250 xFrzb    PQLVANEEYI  IMGYEDKERT  RLLLVEGSLA  EKWRDRLAKK  VKRWDQKLRR   296
    bFrzb    PPLNVNEEYL  IMGYEDEERS  RLLLVEGSIA  EKWKDRLGKK  VKRWDMKLRH   295
    hFRZB    PPLNVNEEYI  IMGYEDEERS  RLLLVEGSIA  EKWKDRLGKK  VKRWDMKLRH   295

Consensus    PPLNVNEEYI  IMGYEDEERS  RLLLVEGSIA  EKWKDRLGKK  VKRWDMKLRH   300 xFrzb    -------PRK  SKDPVAPIPN  KNSNSRQARS                           319
    bFrzb    LGLNTSDSSH  SDSTQSQKPG  RNSNSRQARN                           325
    hFRZB    LGLSKSDSSN  SDSTQSQKSG  RNSNPRQARN                           325

Consensus    LGL..SDSS.  SDSTQSQKPG  RNSNSRQARN                           330
```

*FIG. 4*

ISOLATION AND USE OF TISSUE GROWTH-INDUCING FRZB PROTEIN

RELATED APPLICATIONS

This application is a continuation of prior application 08/729,452 filed Oct. 11, 1996 now abandoned.

FIELD OF THE INVENTION

The present invention relates to a protein isolated from cartilage capable of inducing skeletal morphogenesis, embryonic pattern formation and tissue specification. More particularly, the invention relates to the Frzb protein which induces in vivo cartilage, bone, neural and muscle tissue growth.

BACKGROUND OF THE INVENTION

The discovery and identification of diffusible factors that regulate skeletal morphogenesis have dramatically improved our understanding of the molecular events governing skeletal pattern formation. Genetic studies have confirmed the importance of these differentiation factors in the formation, growth and maintenance of the skeleton (Erlebacher et al., *Cell*, 80:371–378, 1995). Likewise, non-diffusible molecules, including components of the extracellular matrix and cell surface are essential to patterning processes. One theory proposed for insect systems is that morphogenesis results from the (re)positioning of cells because of inherent characteristics such as differential adhesiveness (Nardi et al., *J. Embryol. Exp. Morphol.*, 36:489–512, 1976). It is presently unknown whether analogous events occur in mammalian skeletal pattern formation.

In *Drosophila melanogaster*, the cuticle contains hairs and bristles arranged in a defined polarity, of which the pattern and orderly alignment reflect the polarity of the wing epidermis (Adler et al., *Genetics*, 126:401–416, 1990). Typically, these structures are aligned in parallel and point in the same direction as the body surface. Several genetic loci associated with epidermal cell polarity have been studied. One of the most thoroughly investigated is the *frizzled* (fz) locus. Frizzled encodes an integral membrane protein having seven potential transmembrane domains. The fz locus is required for cellular response to a tissue polarity signal as well as intercellular transmission of that signal along the proximal-distal wing axis (Vinson et al., *Nature*, 329:549–551, 1987; Vinson et al., *Nature*, 338:263–264, 1989). Mutations of the fz locus result in disruption of both cell-autonomous and noncell-autonomous functions of the fz gene. Strong fz mutations are associated with random orientation of wing hairs, while weaker mutations lead to hair and bristles randomly oriented parallel to neighboring cells with respect to the body axis (Vinson et al., *Nature*, 329:549–551, 1987). Frizzled also regulates mirror-symmetric pattern formation in the *Drosophila* eye (Zheng et al., *Development*, 121:3045–3055, 1995).

The rat and human homologs frizzled-1 and frizzled-2 (fz-1, fz-2) have been cloned and are expressed in a wide variety of tissues including kidney, liver, heart, uterus and ovary (Chan et al., *J. Biol. Chem.*, 267:25202–25297, 1992; Zhao et al., *Genomics*, 27:373–373, 1995). Six novel mammalian frizzled homologs have now been identified (Wang et al., *J. Biol. Chem.*, 271:4468–4476, 1996), each of which appears to be expressed in a distinct set of tissues during development or postnatally.

The basic form and pattern of the skeleton derived from lateral plate mesoderm are first recognizable when mesenchymal cells aggregate into regions of high cell density called condensations which subsequently differentiate into cartilage and bone, and continue to grow by cell proliferation, cell enlargement and matrix deposition. Published PCT Application No. WO 96/14335 discloses the isolation, cloning and in vivo chondrogenic activity of cartilage-derived morphogenetic proteins (CDMPs) which are members of the TGF-β superfamily. Genetic studies have demonstrated that disruption of condensations results in disturbed skeletal phenotypes (Erlebacher et la., *Cell*, 80:371–378, 1995). In humans, limb development takes place over a four week period from the fifth to the eighth week. The upper limbs develop slightly in advance of the lower limbs, although by the end of the period of limb development the two limbs are nearly synchronized. The most proximal parts of the limbs develop somewhat in advance of the more distal parts.

There are few known proteins which induce skeletal morphogenesis, as well as induction of nerve and muscle tissue growth. Such proteins have tremendous therapeutic applications. The present invention provides such a multi-faceted protein.

SUMMARY OF THE INVENTION

One embodiment of the present invention is an isolated polynucleotide having the sequence shown in SEQ ID NO: 1, 3 or 23.

Another embodiment of the invention is isolated Frzb protein having the amino acid sequence shown in SEQ ID NO: 2, 4 or 7. According to one aspect of this preferred embodiment, at least one acidic, basic, uncharged polar, nonpolar or aromatic amino acid in the sequence shown in SEQ ID NO: 2, 4 or 7 is replaced with a different acidic, basic, uncharged polar, nonpolar or aromatic amino acid. Preferably, the protein having the amino acid sequence shown in SEQ ID NO: 2 is obtained by expression of a polynucleotide having the sequence shown in SEQ ID NO: 1. According to another aspect of this preferred embodiment, the protein having the amino acid sequence shown in SEQ ID NO: 4 is obtained by expression of a polynucleotide having the sequence shown in SEQ ID NO: 3. According to yet another aspect of this preferred embodiment, the protein having the amino acid sequence shown in SEQ ID NO: 7 is obtained by expression of a polynucleotide having the sequence shown in SEQ ID NO: 23.

Another embodiment of the invention is an isolated polynucleotide encoding a native Frzb protein and capable of hybridizing to a polynucleotide having the nucleotide sequence shown in SEQ ID NO: 1 at 55° C. in 3×SSC, 0.1% SDS.

The present invention also provides an isolated Frzb protein encoded by a polynucleotide capable of hybridizing to a polynucleotide having the nucleotide sequence shown in SEQ ID NO: 1 at 55° C. in 3×SSC, 0.1% SDS.

Still another embodiment of the invention is a pharmaceutical composition comprising an isolated recombinant Frzb protein having the amino acid sequence shown in SEQ ID NO: 2 obtained by expression of a polynucleotide having the sequence shown in SEQ ID NO: 1, the amino acid sequence shown in SEQ ID NO: 4 obtained by expression of a polynucleotide having the sequence shown in SEQ ID NO: 3, or encoded by a polynucleotide capable of hybridizing to a polynucleotide having the nucleotide sequence shown in SEQ ID NO: 1 at 55° C. in 3×SSC, 0.1% SDS, in a pharmaceutically acceptable carrier. In one aspect of this preferred embodiment, the carrier comprises fibrin glue, freeze-dried cartilage grafts or collagen. The composition may further comprise cartilage progenitor cells, chondroblasts or chondrocytes. Alternatively, Frzb protein may be coated onto or mixed with a resorbable or nonresorbable matrix. In another aspect of this preferred embodiment, Frzb is mixed with a biodegradable polymer.

A further embodiment of the invention is a method of treating a cartilage, bone, nerve or muscle disorder in a mammal in need thereof, comprising the step of administering to the individual an effective cartilage, bone, nerve or muscle-inducing amount of any of the pharmaceutical compositions described hereinabove at the site of the disorder. Preferably, the administering step is intravenous, intrathecal, intracranial or intramuscular at the site of the disorder. Advantageously, the mammal is a human.

Another embodiment of the invention is a method of stimulating cartilage formation in a mammal, comprising the steps of:

combining a protein having the amino acid sequence shown in SEQ ID NO: 2, 4 or 7, or a protein encoded by a polynucleotide capable of hybridizing to a polynucleotide having the nucleotide sequence shown in SEQ ID NO: 1 at 55° C. in 3×SSC, 0.1% SDS, with a matrix to produce a product that facilitates administration of the protein; and implanting the product into the body of a mammal to stimulate cartilage formation at the site of implantation.

Preferably, the matrix comprises a cellular material. Advantageously, the mixing step additionally comprises mixing of viable chondroblasts or chondrocytes. In another aspect of this preferred embodiment, the implanting is subcutaneous or intramuscular. Preferably, the mammal is a human.

Still another embodiment of the invention are isolated antibodies to the proteins having the amino acid sequences shown in SEQ ID NO: 2 or 4. These antibodies may be either polyclonal or monoclonal.

The present invention also provides isolated mammalian Frzb protein having a molecular weight of about 36 kilodaltons.

BRIEF DESCRIPTION OF THE DRAWINGS

FIG. 1 shows the nucleotide (SEQ ID NO: 1) and deduced amino acid sequence (SEQ ID NO: 2) of bovine Frzb. The predicted gene product contains 325 amino acids with a putative signal peptide (boxed). The dashed underline indicates the tryptic peptide sequence used to isolate a cDNA fragment by RT-PCR. Two separate consensus polyadenylation sites are underlined. A "TGA" termination codon is shown in the 5'-untranslated region. The putative signal peptide cleavage site is indicated by the scissors.

FIG. 2A shows a comparison between the deduced amino acid sequences of bovine (SEQ ID NO:2) and human (SEQ ID NO: 4) Frzb. The predicted 23 amino acid signal peptide is boxed. The asterisk indicates a potential N-linked glycosylation site. The putative transmembrane region is underlined and bolded.

FIG. 2B shows a hydropathy plot of human Frzb from the deduced amino acid sequence. The plot was generated by the GeneWorks™ program using the paradigm of Kyte and Doolittle. Hydrophobic residues are in the upper part of the graph. The arrowhead at the amino terminus indicates the potential signal peptide. The putative transmembrane domain is indicated by a downward arrow. N, C, and P are N-glycosylation, casein kinase 2 phosphorylation, and protein kinase C phosphorylation sites, respectively. The stippled bar underneath the plot represents the frizzled-like domain.

FIG. 3 shows an amino acid sequence comparison of the N-terminal domain of bovine (amino acids 35–147 of SEQ ID NO: 2) and human (amino acids 35–147 of SEQ ID NO: 4) Frzb, and their homology with amino acids 111–221 of rat fz-1 (SEQ ID NO: 5) and amino acids 53–163 of *Drosophila* frizzled (SEQ ID NO: 6). Identical residues are denoted by shaded boxes. Gaps indicated by hyphens were introduced to optimize sequence alignment. Asterisks indicate conserved cysteine residues. The numbers to the right indicate amino acid residues for each protein.

FIG. 4 shows an amino acid sequence comparison between *Xenopus* Frzb (SEQ ID NO: 7), bovine Frzb (SEQ ID NO: 2) and human Frzb (SEQ ID NO: 4). Amino acids identical among the three sequences are boxed. A consensus sequence (SEQ ID NO: 8) is shown. The putative signal peptide cleavage site is shown by the pair of scissors.

DETAILED DESCRIPTION OF THE PREFERRED EMBODIMENTS

The present invention includes polynucleotides encoding Frzb protein isolated from various mammalian tissues, as well as the corresponding protein sequences and variations thereof. Bovine and human Frzb proteins exhibit 94% amino acid identity. An orthologue of Frzb protein, Xfrzb, is also present in *Xenopus laevis* embryos and exhibits about 92% amino acid identity to the corresponding mammalian Frzb proteins in the conserved frizzled-related domain. Bovine articular cartilage extracts were prepared to characterize protein fractions capable of inducing cartilage formation when implanted subcutaneously into rats (in vivo chondrogenic activity). Trypsin digestion of highly purified chondrogenic protein fractions followed by polymerase chain reaction (PCR) using degenerate oligonucleotide primers derived from a 30 residue tryptic peptide of the purified protein led to identification of a cDNA encoding a 36 kDa protein. The amino-terminal domain of the deduced amino acid sequence exhibited about 50% amino acid identity to the corresponding region of the *Drosophila* gene *frizzled* which is implicated in the specification of hair polarity during development. Because of its homology to frizzled, the protein was named Frzb.

The nucleotide and protein sequences of bovine Frzb are set forth in SEQ ID NOS: 1 and 2, respectively. The nucleotide and protein sequences of human Frzb are set forth in SEQ ID NOS: 3 and 4, respectively. The Frzb protein sequences of the invention have the sequences shown in SEQ ID NOS: 2 and 4, or sequence variations thereof which do not substantially compromise the ability of these proteins to induce cartilage, bone, muscle and nerve tissue induction. It will be appreciated that Frzb proteins containing one or more amino acid replacements in various positions of the sequences shown in SEQ ID NOS: 2 and 4 are also within the scope of the invention. Many amino acid substitutions can be made to the native sequence without compromising its functional activity. This assertion is supported by the sequence data shown in FIG. 4. Both the mammalian and *Xenopus* proteins have biological activity. The primary sequence divergence, particularly in the carboxyl terminal region of the molecule that contains the exon-intron boundaries, is wider between the amphibian and mammalian forms of Frzb. These sequence differences do not materially alter the biological activity of the protein.

Variations of these protein sequences contemplated for use in the present invention include minor insertions, deletions and substitutions. For example, conservative amino acid replacements are contemplated. Such replacements are, for example, those that take place within a family of amino acids that are related in the chemical nature of their side chains. The families of amino acids include the basic amino acids (lysine, arginine, histidine); the acidic amino acids (aspartic acid, glutamic acid); the non-polar amino acids (alanine, valine, leucine, isoleucine, proline, phenylalanine, methionine, tryptophan); and the uncharged polar amino acids (glycine, asparagine, glutamine, cysteine, serine, threonine, tyrosine) and the aromatic amino acids (phenylalanine, tryptophan and tyrosine). In particular, it is generally accepted that conservative amino acid replacements consisting of an isolated replacement of a leucine with an isoleucine or valine, or an aspartic acid with a glutamic acid, or a threonine with a serine, or a similar conservative replacement of an amino acid with a structurally related amino acid, in an area outside of the polypeptide's active site, will not have a major effect on the properties of the polypeptide.

In fact, any protein derivative of SEQ ID NOS: 2 and 4, including conservative substitutions, non-conservative substitutions, mixtures thereof, as well as truncated peptides or sequence variations thereof may be tested as described in the following examples to determine their ability to induce cartilage, bone muscle and nerve tissue. Such routine experimentation will enable the skilled artisan to screen any desired Frzb protein.

A portion of the isolated bovine frzb cDNA sequence (SEQ ID NO: 1) was used to screen a human placental cDNA library under high stringency conditions (3×SSC, 0.1% SDS, 55° C.; see Example 3), resulting in isolation of a cDNA (SEQ ID NO: 3) encoding a protein having 94% identity to the bovine protein. The Xenopus cDNA sequence corresponding to the conserved frizzled-related region exhibits greater than 80% nucleotide sequence identity to both mammalian Frzb genes. Thus, any nucleotide sequence capable of hybridizing to the DNA sequence shown in SEQ ID NO: 1 under these high stringency conditions is within the scope of the invention.

Frzb is recovered in 105,000×g supernatants of lysates prepared from Xenopus embryos or Frzb-transfected mammalian cells, indicating that Frzb is a soluble protein. Both mammalian and *Xenopus* Frzb are secreted from *Xenopus* oocytes injected with the respective mRNAs. In addition, secretion of *Xenopus* Frzb in soluble form was shown by incubation of oocytes with $^{35}$S-methionine followed by analysis of culture supernatants by SDS-PAGE. Moreover, mammalian cells transfected with a Frzb expression plasmid secrete Frzb into the culture medium.

Both mammalian and *Xenopus* Frzb were subcloned into the pcDNA3 mammalian expression vector and expressed in *Xenopus* oocytes. This vector contains a CMV promoter which drives expression of the inserted gene. However, other heterologous promoters well known in the art are also contemplated including SV40 and RSV. Bovine and human Frzb were expressed in ATDC5, COS1 and COS 7 cells and partially purified using heparin-Sepharose and Concanavalin A-Sepharose chromatography. The production of Frzb in insect expression systems, particularly baculovirus, is also within the scope of the invention. This protein preparation was used in the functional assays described in the examples presented below. Bovine Frzb was expressed in *E. coli* and purified from inclusion bodies using Ni-NTA affinity chromatography. Many expression vectors suitable for use in eukaryotic expression systems are also within the scope of the present invention, including the LacSwitch™ inducible mammalian expression system (Stratagene) and pcDNA3 (Invitrogen).

In situ hybridization and immunostaining of human embryonic sections demonstrate predominant expression surrounding the chondrifying bone primordia and subsequently in the chondrocytes of the epiphyses in a graded distribution that decreases toward the primary ossification center. Transcripts are present in the craniofacial structures but not in the vertebral bodies. Because it is expressed primarily in the cartilaginous cores of developing long bones during human embryonic and fetal development (6–13 weeks), has in vivo chondrogenic activity and is homologous to *Drosophila frizzled*, Frzb is intimately involved in skeletal morphogenesis via induction of cartilage and bone formation.

As described in the *Xenopus* embryo experiments set forth below (Example X), both bovine and *Xenopus* Frzb induce formation of secondary body axes which contain neural and muscle tissue, indicating that Frzb is an important protein component in the molecular pathway leading to initial specification of muscle and nerve in vertebrates. Further, both bovine and *Xenopus* Frzb induces molecular markers for muscle (myo D, actin) and nerve (NCAM) tissue. This was determined by explanting ventral marginal zones during gastrulation (stage 10), followed by grafting onto oocytes expressing Frzb and culturing for an appropriate period of time. Explants were removed and assayed for expression of the particular marker. Untreated ventral marginal zones did not express these markers. These results have been obtained with both injection of mRNA into developing vertebrate embryos and with Frzb protein secreted from *Xenopus* oocytes. Frzb also interacts with Wnt proteins directly. Wnt proteins are a large class of secreted proteins implicated in a wide variety of differentiation and developmental processes (Cui et al., *Development*, 121:2177–2186, 1995; Bhanot et al., *Nature*, 382:225–230, 1996). When myc-tagged Wnt and Frzb are cotransfected in mammalian cells, Frzb can be co-immunoprecipitated with an antibody directed against myc. If Frzb mRNA is coinjected with Wnt mRNA into *Xenopus* oocytes, Wnt-mediated induction of dorsal markers is blocked. Thus, overexpression of the gene encoding Frzb will induce the formation of nerve and muscle tissue in vertebrates.

Frzb is contemplated for use in the therapeutic induction and maintenance of cartilage, bone, muscle and nerve tissue. For example, local injection of Frzb as a soluble agent is contemplated for the treatment of subglottic stenosis, tracheomalacia, chondromalacia patellae and osteoarthritic disease. Other contemplated utilities include healing of joint surface lesions (i.e. temporomandibular joint lesions or lesions induced post-traumatically or by osteochondritis) using biological delivery systems such as fibrin glue, freeze-dried cartilage grafts and collagens mixed with Frzb and locally applied to fill the lesion. Such mixtures can also be enriched with viable cartilage progenitor cells, chondroblasts or chondrocytes. Repair or reconstruction of cartilaginous tissues using resorbable or non-resorbable matrices (tetracalcium phosphate, hydroxyapatite) or biodegradable polymers (PLG, polylactic acid/polyglycolic acid) coated or mixed with Frzb is also within the scope of the invention. Such compositions may be used in maxillofacial and orthopedic reconstructive surgery. Frzb can also be used as a growth factor for cells of the chondrocyte lineage in vitro. Cells expanded ex vivo can be implanted into an individual at a site where increased chondrogenesis is desired.

The pharmaceutical composition comprising Frzb may also be used to treat or slow neurodegenerative (i.e. Huntington's disease, Alzheimer's disease, spinal cord injuries), myodegenerative (i.e. muscular dystrophy, myasthenia gravis, myotonic myopathies) and osteodegenerative disorders (i.e. osteoporosis, osteitis deformans). A Frzb-containing pharmaceutical composition is administered to an individual in need of facilitated neural, muscle, or bone cell growth in a growth-facilitating amount thereof. The Frzb protein will promote the growth of these tissues. Thus, Frzb is a growth factor or cytokine capable of inducing growth of a variety of tissues. It is also contemplated that Frzb will positively impact the growth of other tissues, including skin and blood vessels. Thus, Frzb-containing compositions may be used for stimulation of wound healing (i.e. lacerations, burns, surgical incisions), promotion of angiogenesis, to prevent rejection in tissue transplantation and as adjuvants to chemotherapy and immunotherapy.

One embodiment of the invention is a pharmaceutical composition comprising the protein shown in SEQ ID NOS: 2 or 4, or sequence variations thereof, in a pharmaceutically acceptable carrier which may be supplied in unit dosage form. Frzb can be administered to an individual in need of facilitated neural, muscle cartilage and bone growth by numerous routes, including intravenous, subcutaneous, intramuscular, intrathecal, intracranial and topical. The compound is combined with a pharmaceutically acceptable carrier prior to administration. Such pharmaceutical carriers are known to one of ordinary skill in the art.

The Frzb compositions for intravenous administration may be in the form of a sterile injectable preparation, such as a sterile injectable aqueous or oleaginous suspension. Frzb may be provided as either a bolus or continuous intravenous, intrathecal or intracranial drip infusion. Because the composition will not cross the blood brain barrier, intrathecal (in the cerebrospinal fluid) or intracranial administration is required for treatment of neurodegenerative disorders. The suspension may be formulated according to methods well known in the art using suitable dispersing or wetting agents and suspending agents. The sterile injectable preparation may also be a sterile injectable solution or suspension in a parenterally acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. for this purpose, any bland fixed oil may be employed including synthetic mono- or diglycerides. In addition, fatty acids such as oleic acid may likewise be used in the preparation of injectable preparations.

The Frzb composition may be in soluble or microparticular form, or may be incorporated into microspheres or microvesicles, including micelles and liposomes.

Contemplated daily dosages of Frzb for parenteral administration to patients with neurodegenerative, myodegenerative, and osteodegenerative disorders are between about 1 µg and about 100 µg. Particularly preferred daily dosages are between about 10 µg and about 50 µg. This dosage can be administered once per day, or split over 2, 3, 4 or more administrations. The exact dosage can be determined by routine dose/response protocols known to one of ordinary skill in the art. In a preferred embodiment, administration of Frzb is continued until no further improvement in the particular disorder is observed.

It is also anticipated that the frzb polynucleotides of the invention will have utility as diagnostic reagents for detecting genetic abnormalities associated with genes encoding Frzb. Such genetic abnormalities include point mutations, deletions or insertions of nucleotides. Diagnostic testing is performed prenatally using material obtained during amniocentesis or chorionic villus sampling. Any of several genetic screening procedures may be adapted for use with probes enabled by the present invention, including restriction fragment length polymorphism (RFLP) analysis, ligase chain reaction or PCR. Mutations in this gene indicate an increased risk of developmental abnormalities.

Drug screening assays can be used to identify activators or inhibitors of the Frzb protein. For example, Frzb is incubated with a particular drug prior to the in vivo chondrogenesis assay described in Example 1 and compared to a control containing Frzb alone. An increase in cartilage growth in the presence of a drug compared to Frzb alone indicates activation of Frzb, while a decrease indicates inhibition of Frzb activity.

The isolation and partial sequencing of a chondrogenic activity present in bovine cartilage is described below.

EXAMPLE 1

Preparation and Activity of Articular Cartilage Extracts

To characterize factors responsible for cartilage inductive activity in articular cartilage, a protein fraction containing potent cartilage inductive activity was isolated as described in PCT Publication No. WO 96/14335, the entire contents of which are hereby incorporated by reference. Articular (metatarsophalangeal joints) cartilage extracts were prepared from newborn calves as described (Chang et al., *J. Biol. Chem.*, 269:28227–28234, 1994, hereby incorporated by reference) to characterize protein fractions with in vivo chondrogenic activity. Briefly, tissues were finely minced and homogenized with a Polytron (top speed, 2×30 seconds) in 20 volumes 1.2 M guanidine hydrochloride, 0.5% CHAPS, 50 mM Tris-HCl, pH 7.2, containing protease inhibitors and extracted overnight at 4° C. as described by Luyten et al. (*J. Biol. Chem.*, 264:13377, 1989), which is hereby incorporated by reference. Extracts were concentrated and exchanged with 6 M urea by diafiltration using an Ultrasette™ (Filtron Technology, Inc., Mass.) and applied to a 0.5 l heparin-Sepharose (Pharmacia/LKB, Piscataway, N.J.) column. the column was washed with 5 bed volumes of 6 M urea, 50 mM Tris-HCl, pH 7.4, 0.15 M NaCl, then eluted with 2 volumes 1 M NaCl in the same buffer.

In vivo chondrogenic activity was assayed in a subcutaneous implantation model in rats using a collagenous carrier (Luyten et al., *Arch. Biochem. Biophys.*, 267:416–425, 1988; Luyten et al., ibid., hereby incorporated by reference). Briefly, a portion of each fraction was assayed by reconstitution with 25 mg guanidine-insoluble collagenous residue of demineralized rat bone matrix according to procedures described by Luyten et al. (ibid.). Implants were recovered after 10 days and alkaline phosphatase activity was measured as a biochemical indicator or cartilage and/or bone formation. Implants were also examined histologically for evidence or cartilage formation using standard procedures known to those of ordinary skill in the art.

The 1 M NaCl eluate of articular cartilage, which contained biological activity, was concentrated by diafiltration and applied to a Sephacryl S-200 HR gel filtration column (XK 50/100, Pharmacia/LKB). After molecular sieve chromatography, bioactive fractions were pooled and exchanged into 50 mM HEPES, pH 7.4, containing 0.15 M NaCl, 10 mM $MgSO_4$, 1 mM $CaCl_2$ and 0.1% (w/v) CHAPS using Macrosep™ concentrators (Filtron). The equilibrated sample was mixed with 1 ml ConA Sepharose (Pharmacia-LKB) previously washed with 20 volumes of the same buffer according to the procedure described by Paralkar et al. (*Biochem. Biophys. Res. Commun.*, 131:37, 1989, hereby incorporated by reference). After overnight incubation on an orbital shaker at 4° C., the slurry was packed into disposable 0.7 cm ID Bio-Rad columns (Bio-Rad, Hercules, Calif.) and washed with 20 volumes of the HEPES buffer to remove unbound proteins. Bound proteins were eluted with 20 volumes of the same buffer containing 0.5 M methyl-D-mannopyranoside. The eluate was concentrated to 200 µl using Macrosep™ concentrators. Macromolecules were precipitated with 9 volumes of absolute ethanol at 4° C. overnight. The precipitate was redissolved in 1 ml 6 M urea, 50 mM Tris-HCl, pH 7.4. Bioactive bound protein was mixed with 2×Laemmli SDS sample buffer (without reducing agents) and analyzed by 12% preparative SDS-PAGE. Gel elution of the separated protein fractions and testing for biological activity was performed as described by Luyten et al. (ibid.). Protein fractions from the 36–40 kDa region were obtained for bioassay by gel elution following SDS-polyacrylamide gel electrophoresis (SDS-PAGE) and were found to be chondrogenic.

Primary sequencing data from the bioactive fractions were determined by transfer to PVDF membranes for amino terminal sequencing (Moos et al., *J. biol. Chem.*, 263:6005–6008, 1988) or to nitrocellulose membranes for trypsin digestion as previously described (Aebersold et al., *Proc. Natl. Acad. Sci. USA*, 84:6970–6974, 1987; Tempst et al., *Electrophoresis*, 11:537–553, 1990, both of which are hereby incorporated by reference). Tryptic peptides were separated by reverse-phase high performance liquid chromatography (HPLC) (Epifano et al., *Development*, 121:1947–1956, 1995, incorporated by reference), and the sequence of individual peptides was determined using an Applied Biosystems Model 477A sequencer (Applied Biosystems, Foster City, Calif.) with modifications (Tempst et al., ibid.; Tempst et al., *Anal. Biochem.*, 183:290–300, 1989, incorporated by reference).

EXAMPLE 2

Reverse Transcriptase-polymerase Chain Reaction (RT/PCR)

Two degenerate oligonucleotide primers corresponding to the amino- and carboxyl-terminus of the 30 amino acid tryptic peptide 323 (ETVNLYTSAGCLCPPLNVNEEYLIMGYEFP; SEQ ID NO: 9) were used in RT/PCR to clone cDNAs corresponding to peptide 323:

```
323S:  5'-GA(A/G)AC(A/C/T)GT(C/G)AA(C/T)CT(C/G/T)TA-      (SEQ ID NO:10)
       (C/T)AC(A/C/G/T)-3'; and

323AS: 5'-(A/G)AA(C/T)TC(A/G)TA(A/C/G/T)CCCAT(A/C/G/T)AT-3'  (SEQ ID NO:11)
```

Figure 1:
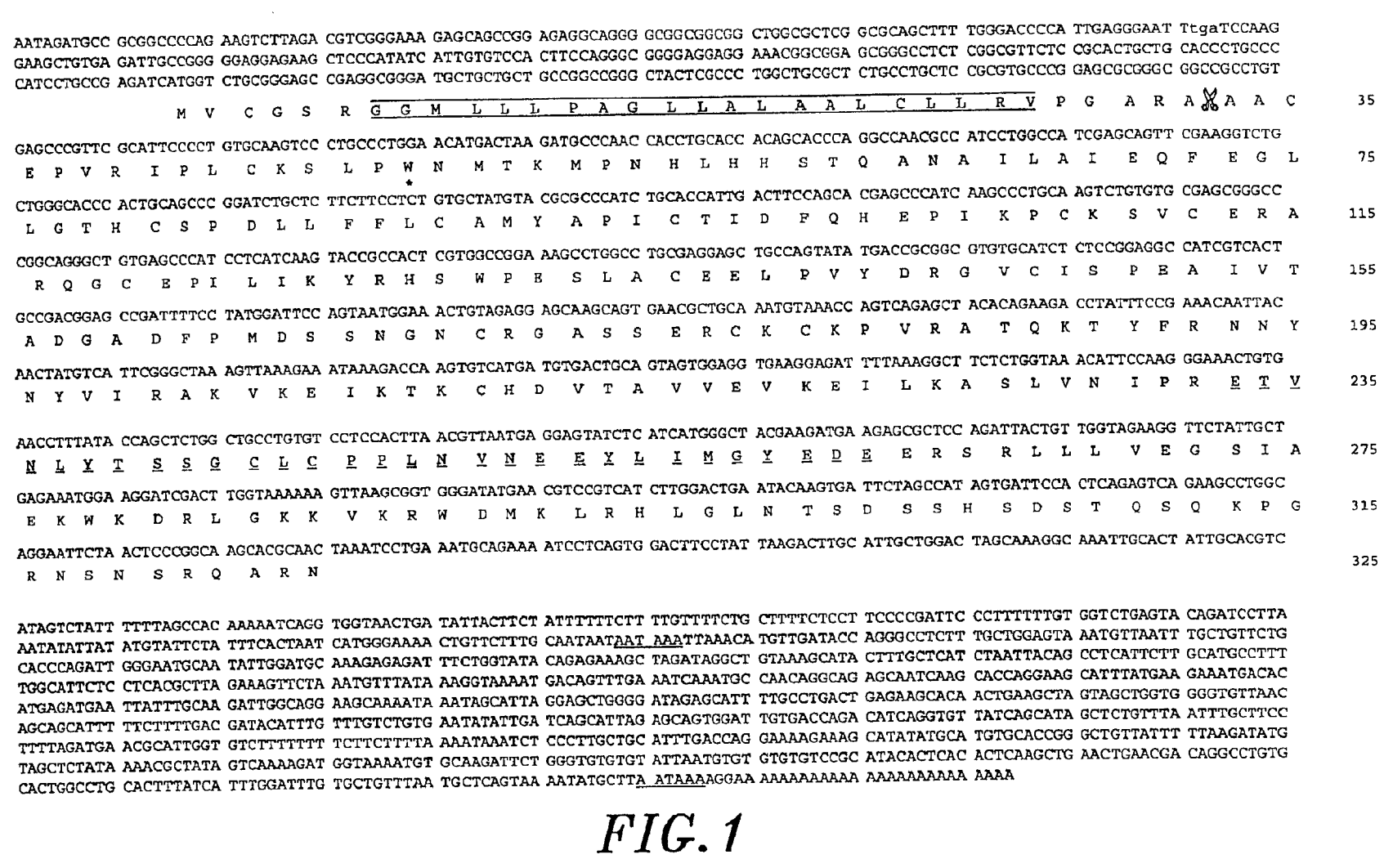

For RT/PCR, first strand cDNA synthesis was performed with 1 µg poly(A)⁺ or 5 µg total RNA prepared from bovine articular chondrocytes using random hexanucleotide primers from the cDNA Cycle™ kit (Invitrogen corp., San Diego, Calif.) or 323AS. 323/323AS primer pairs were used in 30 cycles at 94° C. for 1 min, 50° C. for 1 min and 72° C. for 30 sec. PCR products were purified through a Probind™ membrane (Millipore), followed by subcloning with the TA Cloning™ System (Invitrogen). This yielded a 90 base pair (bp) DNA fragment encoding the proper peptide sequence (dashed underline, FIG. 1). The amino acid sequence deduced from the PCR product was the same as the tryptic peptide sequence.

Other tryptic fragments were also sequenced by Edman degradation and had the following sequences: GVCISPEAIVTA(D or H)GADFPM (SEQ ID NO: 12); QGCEPILIK (SEQ ID NO: 13); QGCEPILICAWPPLY (SEQ ID NO: 14) and ETVNLYTSAGCLCPPLNVNEEYLIMGYE (SEQ ID NO: 15). SEQ ID NO: 12 containing the D residue corresponds to amino acids 145–163 of SEQ ID NO: 2. SEQ ID NO: 13 corresponds to amino acids 117–125 of SEQ ID NO: 2. SEQ ID NO: 14 is not found within SEQ ID NO: 2. SEQ ID NO: 15 corresponds to the sequence found within SEQ ID NO: 2 (ETVNLYTSSGCLCPPLNVNEEYLIMGYE; SEQ ID NO: 16) except for position 9 at which there is an alanine in SEQ ID NO: 13 and a serine in SEQ ID NO: 16. The proteins containing these amino acid sequences are most likely structurally and functionally related to the isolated cDNA. These peptides are useful in the design of oligonucleotide probes or in the generation of antisera for nucleic acid hybridization and expression cloning, respectively, of other members of the Frzb protein family. This will allow isolation of other Frzb-related proteins from any vertebrate species.

cDNA clones were isolated and sequenced as described in the following example.

EXAMPLE 3

Isolation and Sequencing of cDNA Clones

Bovine articular cartilage total RNA was isolated as described (Luyten et al., *Exp. Cell Res.*, 210:224–229, 1994, incorporated by reference). Poly(A)⁺ RNA was isolated using the PolyATractm magnetic bead system (Promega, Madison, Wis.). A cDNA library was constructed in a UNIZAP™XR (Stratagene, La Jolla, Calif.) starting from bovine articular cartilage poly(A)⁺ RNA. The non-degenerate oligonucleotides designed from the 90 base pair fragment amplified by RT/PCR in Example 2 used to screen the articular cartilage cDNA library were:

```
323.23: 5'-GCTCTGGCTGCCTGTGTCCTCCACTTAACG-3'   (SEQ ID NO:17)

323.40: 5'-CCTCCACTTAACGTTAATGAGGAGTATCTC-3'   (SEQ ID NO:18)
```

Plaques hybridizing to both oligonucleotides were further purified using standard plaque hybridization procedures (Sambrook et al., *Molecular Cloning: A Laboratory Manual*, 2nd ed., Cold Spring Harbor laboratory Press, Cold Spring Harbor, N.Y., incorporated by reference). A 2.4 kb clone contained a single open reading frame (ORF) with two separate consensus polyadenylation sites and a poly A tail (FIG. 1). A 1.3 kb clone contained a single polyadenylation signal, a short poly A tail and a short 5'-noncoding region. Three other clones lacked the poly A tail but contained longer 5' ends. Because Northern analysis using a bovine cDNA probe revealed corresponding mRNA expression in placenta, a human placental cDNA library was screened to isolate the human orthologue.

Four clones ranging from 1.3 to 1.6 kb were analyzed and all contained the same open reading frame. All clones contained a consensus translation initiation site (Kozak, *J. Biol. Chem.*, 266:19867–19870, 1991) and an in-frame termination codon situated 144 base pairs upstream of the methionine start codon (FIG. 1). The size difference between the bovine and human cDNA inserts (2.4 kb vs. 1.3 kb) is due to a longer 3' untranslated region in the bovine clone (FIG. 1). Based on sequences from these overlapping cDNA clones, the predicted size of both the human and bovine protein is 325 amino acids (FIG. 2A) (36.2 kDa).

The bovine and human amino acid sequences are 94% identical. The deduced protein sequence of both the human and bovine cDNA revealed at lest four structural domains (FIGS. 1, 2A, 2B). An amino-terminal hydrophobic stretch of 25 amino acids immediately downstream of the initiation methionine likely represents a signal peptide (von Heijne, *Nucl. Acids Res.*, 14:4683–4690, 1986). A second hydrophobic region of 24 amino acids (residues 75–98), which represents a putative transmembrane domain, is followed be a region containing several potential serine/threonine phosphorylation sites and a serine-rich carboxyl-terminal domain (residues 301–325). Both homologs contain an N-linked glycosylation site at Asn 49, which is amino-terminal of the putative transmembrane domain. A potential C-terminal glycosylation site in the bovine protein was not present in the human homolog.

A search of the Gen Bank™ data base using the BLAST network service at the national Center for Biotechnology Information (NCBI) (Altschul et al, *J. Mol. Biol.*, 215:403–410, 1990) indicated that Frzb has significant identity (about 50%) in the amino-terminal region (from amino acid 35–147) to *Drosophila frizzled* and rat fz proteins (FIG. 3). The homologous region begins shortly after the cleavage site of the predicted signal sequence. The 10 cysteine residues in this region are conserved.

Following isolation of the bovine cDNA, PCR was used to generate a 1 kb fragment containing XhoI sites at both ends. This fragment, representing the bovine open reading frame (bORF), was used to screen a human placenta λgt11 cDNA library (Clontech, Palo Alto, Calif.). Approximately $7\times10^5$ plaques from the bovine library and $3\times10^5$ plaques from the human library were screened. Hybridizations were performed for 24 hours at 42° C. in 6×SSC, 1×Denhardt's solution, 0.01% yeast tRNA and 0.05% sodium pyrophosphate. The membranes were washed to a final stringency of 3×SSC, 0.1% SDS at 55° C. for 15 minutes (3×SSC=50 mM sodium citrate, pH 7.0, 0.45 M NaCl).

Sequencing was performed using the dideoxy chain termination method (Sanger et al., *Proc. Natl. Acad. Sci. USA*, 74:5463–5467, 1977) and Sequenase™ Version 2.0 DNA polymerase according to the manufacturer's instructions (United States Biochemical Corp., Cleveland, Ohio). The sequencing data were obtained by primer walking and from subclones of restriction fragments into pBluescript SKII (Stratagene). Compressions were resolved by performing the sequencing reactions in the presence of 7-deaza-GTP (U.S. Biochemical).

Bovine Frzb was expressed in *E. coli* and purified therefrom as described below.

EXAMPLE 4

Frzb Protein Expression and Antibody Production

The full-length bovine frzb gene was subcloned into the pcDNA3 mammalian expression vector (Invitrogen, San Diego, Calif.) under control of the CMV promoter and used to transfect ATDC5, COS-1 (ATCC CRL 1650) and COS-7 (ATCC CRL 1651) cells using the LipofectAMINE™ reagent (GIBCO/BRL, Gaithersburg, Md.) according to the manufacturer's instructions. A soluble, secreted Frzb protein was obtained from culture supernatants and partially purified by heparin-Sepharose and Concanavalin A-Sepharose chromatography.

The bovine frzb open reading frame was subcloned in the proper orientation into the XhoI site of pET-28a(+) (Novagen, Madison, Wis.) which contains an amino-terminal stretch of six histidine residues to facilitate purification of the expressed protein as well as a T7 tag for immunodetection. The pET-bORF construct was used in the *E. coli*-based pET System™ to obtain bovine Frzb fusion protein. Purification of protein product from inclusion bodies with Ni-NTA affinity chromatography (QIAGEN) was performed using decreasing pH steps according to the manufacturer's instructions. The affinity purified protein was visualized as a major band following Coomassie blue staining after SDS-PAGE. The identity of the fusion product was verified by immunoblotting using a T7 monoclonal antibody. Rabbits were immunized with Frzb fusion protein for 6 months, 250 μg protein per boost, total of 10 injections. Following immunization, several rabbits were subsequently immunized with a synthetic peptide of 12 amino acids (residues 51–61 of FIG. 1) coupled to keyhole limpet hemocyanin (KLH) through a carboxyl-terminal cysteine. The resulting antisera were screened and titered in immunoblots using the Western-Light Plus™ kit (TROPIX, Mass.) according to the manufacturer's protocol. Briefly, membranes were incubated overnight in blocking buffer (BF) containing 0.6% I-BLOCK™ (TROPIX) in phosphate buffered saline (PBS) and 0.1% Tween-20. The antiserum was diluted from 1:250 to 1:10,000 in BF. The membranes were washed three times for 5 min in BF after each incubation step. The membranes were incubated with secondary antibody at a dilution of 1:20,000 for 30 min, followed by AVDIX™ (enzyme conjugate) incubation for 20 min. Blots were developed using the CSPD™ chemiluminescent substrate (TROPIX) and exposed to Kodak XAR-5 film for 1 to 10 min. Antiserum N374-PEP afforded the optimal signal to noise ratio in Western blots and was thus selected for further studies and immunohistochemical staining. This antibody detected a band migrating at the same apparent molecular weight as the Ni-NTA affinity purified protein as determined by Western blot analysis. This method can be used to generate antiserum to human Frzb, as well as any desired immunogenic fragment of bovine or human Frzb.

Monoclonal antibodies to Frzb can also be generated using conventional hybridoma technology known to one of ordinary skill in the art. Briefly, three mice are immunized with 25 μg recombinant Frzb produced as described in above. Mice are inoculated at 3 week intervals with 20 μg Frzb per mouse (½ subcutaneously and ½ intraperitoneally). Serum collected from each animal after the first inoculation reacts with Frzb as determined by immunoprecipitation.

Three days after the final inoculation, mice are sacrificed and the spleens harvested and prepared for cell fusion. Splenocytes are fused with Sp2/0 Ag14 myeloma cells (ATCC CRL 1581) with polyethylene glycol (PEG). Following PEG fusion, cell preparations are distributed in 96-well plates at a density of $10^5$ cells per well and selected in hypoxanthine/aminopterin/thymidine (HAT) medium containing 10% fetal calf serum and 100 U/ml interleukin-6. The medium is replaced with fresh HAT medium 10 days after plating. To identify hybridomas producing MAbs which recognized Frzb epitopes, hybridoma supernatants are tested for the ability to immunoprecipitate purified Frzb or to detect Frzb by immunoblotting.

As previously discussed, Frzb is a secreted soluble protein; however, to determine whether it also exists in a membrane-associated form, the following cell fractionation study was performed.

EXAMPLE 5

Cell Fractionation

A full length 2.4 kilobase (kb) BamHI-XhoI fragment of bovine Frzb (FIG. 1) was cloned into the pcDNA3 expression vector (Invitrogen) to generate the construct pFrzb. COS1 cells ($1.6\times10^6$ initial seeding density) were transfected with 10 µg of either pFrzb or the control pcDNA3 vector per 100 mm dish using 120 µl LipofectAMINE™ reagent (GIBCO/BRL, Gaithersburg, Md.). Transfection was carried out for 6 hours in serum-free OPTI-MEM® (GIBCO/BRL). Cells were incubated at 37° C. for 72 hours in serum-free OPTI-MEM® with daily media changes. Conditioned media were then collected and concentrated 20-fold using a Centricon™ 10 microconcentrator (Amicon, Mass.). Cells were scraped from the dishes and resuspended in lysis buffer (10 mM Tris-HCl, 5 mM EDTA, 1 mM phenylmethylsulfonyl fluoride (PMSF)). Cells were lysed using a syringe and a 25-gauge needle and the resulting lysate was collected. The lysate was centrifuged at 3,000×g for 10 min to pellet debris, nuclei and non-lysed cells. The resulting supernatant was centrifuged at 100,000×g for 30 min.

The resulting pellet, containing primarily membrane vesicles, microsomes and other particulates, was extracted successively with: 1) 10 mM Tris-HCl, pH 8.0, 6 M urea; 2) 10 mM Tris-HCl, pH 8.0, 1% Triton X-100, 6M urea; 3) 10 mM Tris-HCl, pH 8.0; and 4) 1% SDS in 1% Triton/6 M urea/10 mM Tris-HCl, pH 8.0. After each extraction, samples were centrifuged at 100,000×g for 30 min. The extracts were then precipitated with an equal volume of 30% trichloroacetic acid (TCA) and re-dissolved in SDS sample buffer. Equal amounts of cytosol, the membrane/particulate fraction and concentrated conditioned media were loaded and separated on 4–20% gradient Tris-glycine gels (Novex, San Diego, Calif.), blotted to Tropifluor™ PVDF membrane (TROPIX) using a GENIE™ electrophoretic blotter (Idea Scientific, Minneapolis, Minn.) and analyzed by immunoblotting as described in Example 4. The primary antiserum (N374-PEP) dilution was 1:1,000. The urea/SDS/Triton extract of the membrane pellet contained most of the Frzb protein. No protein was detected in the supernatants of the transfected cells or in untransfected cells.

Because the protein sequencing data were obtained from partially purified protein preparations of bovine articular cartilage extracts, similar cell fractionation studies were performed on supernatants and cell extracts of primary bovine articular chondrocyte cultures. Cells were grown to confluence in 100 mm dishes in Dulbecco's Modified Eagle's Medium (DMEM) containing 10% fetal bovine serum (FBS), then incubated for 48 hours in serum free OPTI-MEM® in the presence or absence of dextran sulfate (250 µg/ml) to improve recovery of soluble protein. Conditioned media and cell layers were processed as described above. Again, most of the protein was detected in the membrane associated fractions. The addition of dextran sulfate did not change this distribution.

Thus, Frzb exists in both membrane-associated and soluble forms. Recent evidence suggests that the results of cell fractionation studies depend upon the cell or tissue type and are likely related to cell type specific differences in posttranslational proteolytic processing. Frzb is secreted in soluble form in some, but not all, mammalian expression systems. Importantly, Frzb is soluble in frog embryos. It is possible that Frzb may occur, and act, in both soluble and particulate forms. Nonetheless, the observation that Frzb can be secreted is highly significant in that soluble protein factors are more amenable to production and formulation. In secreted proteins, the signal peptide is cleaved from the preprotein to form the biologically active secreted molecule. In the mammalian cell expression systems used herein, cell lysates contained two Frzb bands as visualized by Western blots, one corresponding to the unprocessed protein containing the signal peptide, and one corresponding to the processed protein lacking the signal peptide. When Western blots were performed on a clarified lysate of *Xenopus* embryos, a single protein band was observed.

Localization of mRNA encoding Frzb in human embryos was determined by in situ hybridization as described below.

EXAMPLE 6

In situ Hybridization

Serial sections of human embryos representing various stages of development were used for in vitro hybridization to explore the pattern of Frzb expression during embryonic development. Tissues from human embryos ranging from 6 to 13 weeks of gestation, estimated on the basis of crown-rump length and pregnancy records, were fixed in 4% paraformaldehyde in 0.1 M phosphate buffer (pH 7.2), embedded in paraffin, cut serially at 5–7 µm and mounted on salinated slides. These tissues were obtained from legally sanctioned procedures performed at the University of Zagreb Medical School, Zagreb, Croatia. The procedure for obtaining autopsy materials was approved by the Internal Review Board of the Ethical Committee at the University of Zagreb School of Medicine and the Office of Human Subjects Research of the National Institutes of Health, Bethesda, Md. In situ hybridization was performed as described previously (Pelton et al., *Development*, 106:759–767, 1989; Vukicevic et al., *J. Histochem. Cytochem.*, 42:869–875, 1994). Briefly, after a short prehybridization, sections were incubated overnight at 50° C. in 50% formamide, 10% dextran sulfate, 4×SSC, 10 mM dithiothreitol (DTT), 1×Denhardt's solution, 500 µg/ml freshly denatured salmon sperm DNA and yeast tRNA with 0.2–0.4 ng/ml $^{35}$S-labeled riboprobe ($1\times10^9$ cpm/µg) in a humidified chamber. Since the bovine Frzb open reading frame contained XhoI sites at both ends, this fragment was subcloned in both sense and antisense directions into the XhoI site of pBluescript SKII-vector and riboprobes were made using T7 RNA polymerase according to the manufacturer's instructions (Novagen). After hybridization, the sections were washed to a final stringency of 0.1×SSC, 65° C. for 2×15 min. After dehydration in a graded ethanol series containing 0.3 M ammonium acetate, slides were covered with NTB-2 emulsion (Kodak) and exposed for 1–3 weeks. The slides were then stained with 0.1% toluidine blue, dehydrated, cleared with xylene and mounted with Permount.

Between 6 and 13 weeks, no hybridization was detected in most organs, including kidney, heart, muscle, intestine, liver, brain and lung. In contrast, strong hybridization was seen in the developing appendicular skeleton. At six weeks, Frzb transcripts were clearly visible surrounding the early cartilaginous rudiments of the developing limbs, as shown in the distal parts of the upper limb. Hybridization was apparent between neighboring areas of cartilaginous condensation in developing long bones. Subsequently, expression appeared within the cartilaginous cores of developing long bones. This was apparent in the proximal parts of the upper limb, which are more advanced in developmental state than the distal parts. Frzb was also present in the putative limb primordia, thereby bridging the expression data obtained in early development to the localization in developing limbs. Additional experiments in developing limbs have revealed expression in the precartilaginous condensations and subsequently in the future joint interzones.

In addition, Frzb was detected in the cartilage anlagen of several craniofacial bones and the epiphysial ends of the rib cage, while no signal was detected in the vertebral bodies at 6 weeks. At 13 weeks of gestation, Frzb transcripts were present in early chondroblasts of the tarsal bones of the foot, the carpal bones of the hand and the epiphysis of long bones. A striking feature of the expression pattern at this developmental stage was the presence of a graded distribution, most prominent in the phalanges. The highest level of expression was observed at the epiphyses of long bones and at the periphery of cuboidal bones. The expression level then decreased with the appearance of chondrocyte hypertrophy and vascular invasion and appeared to be absent in the primary centers of ossification. Interestingly, at this stage of development, several layers of chondroblasts adjacent to the joint space did not show detectable transcripts. In sharp contrast to the prominent expression observed in other skeletal structures, no expression was apparent in the vertebral bodies at the stages examined.

A *Xenopus laevis* orthologue of Frzb (Xfrzb) was isolated as described below.

EXAMPLE 7

Isolation of XFrzb cDNA

The primers 5'-TGGAACATGACTAAGATGCCC-3' (SEQ ID NO: 19) and 5'-CATATACTGGCAGCTCCTCG-3' (SEQ ID NO: 20) were used to label a region of the bovine Frzb CDNA sequence having a high degree of sequence identity to related genes from human and avian sources. 106 plaques from a Stage 20 *Xenopus* CDNA library prepared in ISH-lox (Novagen, Madison, Wis.) were screened at low stringency (final stringency 35=BOC in 20 mM $Na_2HPO_4$, pH. 7.2, 1 mM EDTA, 1% SDS) and purified plaques were characterized by direct sequencing (Wang et al., *BioTechniques,* 130–135, 1995). One 498 bp clone was 92% identical to a region of the bovine sequence. Two oligonucleotides, 5'-GTCTTTTGGGAAGCCTTCATGG-3' (SEQ ID NO: 21) and 5'-GCATCGTGGCATTTCACTTTCA-3' (SEQ ID NO: 22), corresponding to the 5' and 3' regions of this partial length clone, were used to screen duplicate lifts from a stage 13 library (Richter et al., *Proc. Natl. Acad. Sci. USA,* 8086–8090, 1988). Plaques that hybridized to both oligonucleotides were further analyzed. Several clones containing a complete open reading frame were identified and sequenced. Two closely similar clones were isolated and one of these was chosen for further study. The nucleotide and deduced amino acid sequences of this Xfrzb clone is shown in SEQ ID NOS: 23 and 7, respectively.

Expression of Xfrzb was analyzed by in situ hybridization as described in Example 6. Expression begins early in gastrulation and continues as the embryo matures. Thus, it is present when many of the most important events in the establishment of the overall body plan of the developing embryo occur. It is expressed initially in the organizer region, extending beyond it during gastrulation. At the end of gastrulation, expression in this region abruptly ceases and then appears in primordial head mesoderm. Expression then becomes more localized, ultimately to a region corresponding to the developing pituitary gland. These observations are consistent with an important role in the induction of the nervous system and axial musculature, from which the majority of skeletal muscle is derived. Its expression in the pituitary suggests a prominent role in defining anterior mesodermal structures, including the pituitary itself.

EXAMPLE 8

Immunohistochemical Staining

Tissue sections were stained using the Vectastain® elite ABC kit (Vector Laboratories, Burlingame, Calif.) according to the manufacturer's protocol. All embryos were embedded in JB-4 resin (Polysciences, Warrenton, Pa.). For conventional histological analysis, 1–3=B5m sections were cut and stained with hematoxylin and eosin. Before staining, tissue sections were pretreated with chondroitinase ABC for 1 hour. The sections were blocked with PBS and 10% goat serum for 30 min, then incubated for 1 hour with primary antiserum (N374-PEP) at a dilution of 15 $\mu$g/ml in PBS containing 0.5% goat serum. In the controls, the primary antibody was replaced with normal pre-immune rabbit serum or secondary antibody alone.

Immunohistochemical staining confirmed the presence of protein in developing skeletal structures, appearing within the cartilaginous cores of the developing long bones. The graded mRNA expression pattern detected by in situ hybridization, most prominent in the phalanges, was paralleled by the protein distribution.

EXAMPLE 9

Ectopic expression of Frzb in *Xenopus* embryos

Ectopic expression in developing *Xenopus* embryos induced formation of secondary body axes which contained neural and muscle tissue, but no notochord. This assay is an extremely stringent and specific test for the ability of a gene product to initiate a complex program of developmental events and indicates that Frzb can initiate the synthesis of nerve and muscle tissue. Further, overexpression of Xfrzb in explants fated to develop into ventral tissue induced molecular markers of muscle and nerve tissue.

Ultraviolet irradiation interrupts the normal mechanism for establishment of the dorso-anterior body axis, so that treated embryos did not develop dorsal structures (i.e. head, somites, neural tube, notochord) or the tissues comprising them. When irradiated enzymatically defolliculated embryos were injected with 50 $\mu$g mRNA encoding Xfrzb, a body axis was restored. The reconstituted axis contained a neural tube and dysmorphic somites, but no notochord. This experiment is an even more demanding test of the ability of a protein to initiate a complex developmental program. If a truncated construct, containing only the putative extracellular and transmembrane regions of the molecule, was used for injection with mRNA at the two cell stage of one blastomere, one half of the embryo appeared to develop normally, while the other was devoid of both muscle and neural tube; the notochord was normal bilaterally. This study evaluated the effects of ablating the function of Xfrzb, based on the premise that the defective molecule could act as a competitive inhibitor of endogenous Frzb. The effect produced by the defective Frzb was in essence the converse of what is observed in the unmodified gene is overexpressed.

EXAMPLE 10

Treatment of Deep Knee Defects with Frzb

A young patient having a large defect in the articular surface of the knee joint is identified. A periosteal flap is obtained from the bone beneath the joint surface of rib cartilage according to standard surgical procedures. The tissue flap is pre-incubated in a solution containing recombinant human or bovine Frzb protein. The Frzb-treated periosteal flap is then attached over the lesion in the articular surface of the knee joint by a sewing procedure using, for example, resolvable material. The joint is then closed and injected with a solution containing bovine, human or Xenopus Frzb protein in a pharmaceutically acceptable carrier. Injections are administered until cartilage repair is complete. The patient notices markedly less joint pain as the cartilage repair process progresses. Examination by arthroscopy indicates repair of the lesion within several weeks following the initial procedure.

It is also contemplated that gene therapy protocols based on expression of Frzb cDNAs or genomic constructs can be used to facilitate in vivo cartilage, bone, muscle and nerve repair. Therapy may be achieved by genetically altering synoviocytes, periosteal cells, chondrocytes, myoblasts, osteoblasts or neural cells by transfection or infection with recombinant constructs directing expression of Frzb. Such altered cells can then be returned to the appropriate in vivo location. Gene transfer can be performed using numerous vectors well known in the art, including retroviruses, adenoviruses, herpesviruses and adeno-associated viruses.

Both in vivo and ex vivo approaches are anticipated for continuous delivery of Frzb for treating neuro-, myo-, osteo- and chondrodegenerative disorders. In addition, inducible promoter constructs may be employed in gene therapy applications of the present invention.

EXAMPLE 11

Treatment of Duchenne Muscular Dystrophy (DMD)

An individual with DMD is intramuscularly administered 50–100 µg human bovine, human or Xenopus Frzb per day at various locations. Increase in muscle tone and control occurs over the course of several weeks.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. An isolated recombinant Frzb protein having the amino acid sequence shown in SEQ ID NO: 7, wherein said Frzb protein induces the formation of secondary body axes in Xenopus embryos.

2. The isolated protein having the amino acid sequence shown in the SEQ ID NO: 7 of claim 1, wherein said protein is obtained by expression of a polynucleotide having the sequence shown in SEQ ID NO: 23.

3. An isolated recombinant Frzb protein having the amino acid sequence shown in SEQ ID NO: 7, wherein at least one acidic amino acid contained therein is replaced with a different acidic amino acid and wherein said Frzb protein induces the formation of secondary body axes in Xenopus embryos.

4. An isolated recombinant Frzb protein having the amino acid sequence shown in SEQ ID NO: 7, wherein at least one basic amino acid contained therein is replaced with a different basic amino acid and wherein said Frzb protein induces the formation of secondary body axes in Xenopus embryos.

5. An isolated recombinant Frzb protein having the amino acid seciuence shown in SEQ ID NO: 7, wherein at least one nonpolar amino acid contained therein is replaced with a different nonpolar amino acid and wherein said Frzb protein induces the formation of secondary body axes in Xenopus embryos.

6. An isolated recombinant Frzb protein having the amino acid sequence shown in SEQ ID NO: 7, wherein at least one uncharged polar amino acid contained therein is replaced with a different uncharged polar amino acid and wherein said Frzb protein induces the formation of secondary body axes in Xenopus embryos.

7. An isolated recombinant Frzb protein having the amino acid sequence shown in SEQ ID NO: 7, wherein at least one aromatic amino acid contained therein is replaced with a different aromatic amino acid and wherein said Frzb protein induces the formation of secondary body axes in Xenopus embryos.

8. An isolated Frzb protein encoded by a polynucleotide having the sequence shown in SEQ ID NO: 23.

9. Isolated Xenopus Frzb protein having a molecular weight of about 36 kilodaltons as determined from its deduced amino acid sequence having the amino acid sequence shown in SEQ ID NO: 7.

10. An isolated recombinant Frzb protein containing amino acids 33–319 of SEQ ID NO: 7.

* * * * *

UNITED STATES PATENT AND TRADEMARK OFFICE
CERTIFICATE OF CORRECTION

PATENT NO. : 6,884,871 B2
DATED : April 26, 2005
INVENTOR(S) : Luyten et al.

It is certified that error appears in the above-identified patent and that said Letters Patent is hereby corrected as shown below:

Title page,
Item [73], Assignee, delete "The United States of America as represented by the Department of Health and Human Services" and insert -- Government of the United States of America as represented by the Secretary, Department of Health and Human Services --.
Item [56], References Cited, OTHER PUBLICATIONS,
"Bouwmeester T., et al." reference, after "organizer" delete "," and insert -- . --.
"Camac, G., et al." reference, delete "Siemois" and insert -- Siamois --.
"Chan, S.D.H., et al." reference, after "Biol" insert -- . --.
"Christian, J.L., et al." reference, delete "Spermann" and insert -- Spemann --.
"Epifano, O., et al." reference, after "mouse" delete "cogenesis" and insert -- oogenesis --.
"Erlebacher, A.," reference, after "Development" insert -- . --.
"Finch, P.W., et al." reference, delete "moelcular" and insert -- molecular --; and after "secreted" delete "." and insert -- , --.
"Hoppler et al." reference, after "Hoppler" insert -- , --; and delete "Induction" and insert -- induction --.
"Lemaire, P., et al." reference, delete "Siarnois" and insert -- Siamois --.
Item [57], ABSTRACT,
Line 3, delete "CDNA" and insert -- cDNA --.
Line 4, delete "frzb" and insert -- Frzb --.

Column 41,
Line 23, delete "seciuence" and insert -- sequence --.

Signed and Sealed this

Seventh Day of February, 2006

JON W. DUDAS
*Director of the United States Patent and Trademark Office*

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
      (A) LENGTH: 2374 base pairs
      (B) TYPE: nucleic acid
      (C) STRANDEDNESS: single
      (D) TOPOLOGY: linear (ix) FEATURE:
      (A) NAME/KEY: Coding Sequence
      (B) LOCATION: 256...1230
      (D) OTHER INFORMATION:

(xi) SEQUENCE DESCRIPTION: SEQ ID NO: 1:

```
AATAGATGCC GCGGCCCCAG AAGTCTTAGA CGTCGGGAAA GAGCAGCCGG AGAGGCAGGG      60

GCGGCGGCGG CTGGCGCTCG GCGCAGCTTT TGGGACCCCA TTGAGGGAAT TTGATCCAAG     120

GAAGCTGTGA GATTGCCGGG GGAGGAGAAG CTCCCATATC ATTGTGTCCA CTTCCAGGGC     180

GGGGAGGAGG AAACGGCGGA GCGGGCCTCT CGGCGTTCTC CGCACTGCTG CACCCTGCCC     240

CATCCTGCCG AGATC ATG GTC TGC GGG AGC CGA GGC GGG ATG CTG CTG CTG     291
                Met Val Cys Gly Ser Arg Gly Gly Met Leu Leu Leu
                  1               5                  10

CCG GCC GGG CTA CTC GCC CTG GCT GCG CTC TGC CTG CTC CGC GTG CCC      339
```

```
                                                                     -continued Pro Ala Gly Leu Leu Ala Leu Ala Ala Leu Cys Leu Leu Arg Val Pro
             15                  20                  25

GGA GCG CGG GCG GCC GCC TGT GAG CCC GTT CGC ATT CCC CTG TGC AAG     387
    Gly Ala Arg Ala Ala Ala Cys Glu Pro Val Arg Ile Pro Leu Cys Lys
         30                  35                  40

TCC CTG CCC TGG AAC ATG ACT AAG ATG CCC AAC CAC CTG CAC CAC AGC     435
    Ser Leu Pro Trp Asn Met Thr Lys Met Pro Asn His Leu His His Ser
    45                  50                  55                  60

ACC CAG GCC AAC GCC ATC CTG GCC ATC GAG CAG TTC GAA GGT CTG CTG     483
    Thr Gln Ala Asn Ala Ile Leu Ala Ile Glu Gln Phe Glu Gly Leu Leu
                     65                  70                  75

GGC ACC CAC TGC AGC CCG GAT CTG CTC TTC TTC CTC TGT GCT ATG TAC     531
    Gly Thr His Cys Ser Pro Asp Leu Leu Phe Phe Leu Cys Ala Met Tyr
                 80                  85                  90

GCG CCC ATC TGC ACC ATT GAC TTC CAG CAC GAG CCC ATC AAG CCC TGC     579
    Ala Pro Ile Cys Thr Ile Asp Phe Gln His Glu Pro Ile Lys Pro Cys
             95                 100                 105

AAG TCT GTG TGC GAG CGG GCC CGG CAG GGC TGT GAG CCC ATC CTC ATC     627
    Lys Ser Val Cys Glu Arg Ala Arg Gln Gly Cys Glu Pro Ile Leu Ile
         110                 115                 120

AAG TAC CGC CAC TCG TGG CCG GAA AGC CTG GCC TGC GAG GAG CTG CC A    675
    Lys Tyr Arg His Ser Trp Pro Glu Ser Leu Ala Cys Glu Glu Leu Pro
    125                 130                 135                 140

GTA TAT GAC CGC GGC GTG TGC ATC TCT CCG GAG GCC ATC GTC ACT GCC     723
    Val Tyr Asp Arg Gly Val Cys Ile Ser Pro Glu Ala Ile Val Thr Ala
                     145                 150                 155

GAC GGA GCC GAT TTT CCT ATG GAT TCC AGT AAT GGA AAC TGT AGA GGA     771
    Asp Gly Ala Asp Phe Pro Met Asp Ser Ser Asn Gly Asn Cys Arg Gly
                 160                 165                 170

GCA AGT AGT GAA CGC TGC AAA TGT AAA CCA GTC AGA GCT ACA CAG AAG     819
    Ala Ser Ser Glu Arg Cys Lys Cys Lys Pro Val Arg Ala Thr Gln Lys
             175                 180                 185

ACC TAT TTC CGA AAC AAT TAC AAC TAT GTC ATT CGG GCT AAA GTT AAA     867
    Thr Tyr Phe Arg Asn Asn Tyr Asn Tyr Val Ile Arg Ala Lys Val Lys
         190                 195                 200

GAA ATA AAG ACC AAG TGT CAT GAT GTG ACT GCA GTA GTG GAG GTG AAG     915
    Glu Ile Lys Thr Lys Cys His Asp Val Thr Ala Val Val Glu Val Lys
    205                 210                 215                 220

GAG ATT TTA AAG GCT TCT CTG GTA AAC ATT CCA AGG GAA ACT GTG AAC     963
    Glu Ile Leu Lys Ala Ser Leu Val Asn Ile Pro Arg Glu Thr Val Asn
                     225                 230                 235

CTT TAT ACC AGC TCT GGC TGC CTG TGT CCT CCA CTT AAC GTT AAT GAG    1011
    Leu Tyr Thr Ser Ser Gly Cys Leu Cys Pro Pro Leu Asn Val Asn Glu
                 240                 245                 250

GAG TAT CTC ATC ATG GGC TAC GAA GAT GAA GAG CGC TCC AGA TTA CTG    1059
    Glu Tyr Leu Ile Met Gly Tyr Glu Asp Glu Glu Arg Ser Arg Leu Leu
             255                 260                 265

TTG GTA GAA GGT TCT ATT GCT GAG AAA TGG AAG GAT CGA CTT GGT AAA    1107
    Leu Val Glu Gly Ser Ile Ala Glu Lys Trp Lys Asp Arg Leu Gly Lys
         270                 275                 280

AAA GTT AAG CGG TGG GAT ATG AAG CTC CGT CAT CTT GGA CTG AAT ACA    1155
    Lys Val Lys Arg Trp Asp Met Lys Leu Arg His Leu Gly Leu Asn Thr
    285                 290                 295                 300

AGT GAT TCT AGC CAT AGT GAT TCC ACT CAG AGT CAG AAG CCT GGC AGG    1203
    Ser Asp Ser Ser His Ser Asp Ser Thr Gln Ser Gln Lys Pro Gly Arg
                     305                 310                 315

AAT TCT AAC TCC CGG CAA GCA CGC AAC TAAATCCTGA AATGCAGAAA ATCCTCA   1257
    Asn Ser Asn Ser Arg Gln Ala Arg Asn
                 320                 325
```

-continued

```
GTGGACTTCC TATTAAGACT TGCATTGCTG GACTAGCAAA GGCAAATTGC ACTATTGCAC    1317

GTCATAGTCT ATTTTTTAGC CACAAAAATC AGGTGGTAAC TGATATTACT TCTATTTTTT    1377

CTTTTGTTTT CTGCTTTTCT CCTTCCCCCA TTCCCTTTTT TGTGGTCTGA GTACAGATCC    1437

TTAAATATAT TATATGTATT CTATTTCACT AATCATGGGA AAACTGTTCT TTGCAATAAT    1497

AATAAATTAA ACATGTTGAT ACCAGGGCCT CTTTGCTGGA GTAAATGTTA ATTTGCTGTT    1557

CTGCACCCAG ATTGGGAATG CAATATTGGA TGCAAAGAGA GATTTCTGGT ATACAGAGAA    1617

AGCTAGATAG GCTGTAAAGC ATACTTTGCT GATCTAATTA CAGCCTCATT CTTGCATGCC    1677

TTTTGGCATT CTCCTCACGC TTAGAAAGTT CTAAATGTTT ATAAAGGTAA AATGACAGTT    1737

TGAAATCAAA TGCCAACAGG CAGAGCAATC AAGCACCAGG AAGCATTTAT GAAGAAATGA    1797

CACATGAGAT GAATTATTTG CAAGATTGGC AGGAAGCAAA ATAAATAGCA TTAGGAGCTG    1857

GGGATAGAGC ATTTTGCCTG ACTGAGAAGC ACAACTGAAG CTAGTAGCTG TTGGGGTGTT    1917

AACAGCAGCA TTTTTCTTTT GACGATACAT TTGTTTGTCT GTGAATATAT TGATCAGCAT    1977

TAGAGCAGTG GATTGTGACC AGACATCAGG TGTTATCAGC ATAGCTCTGT TTAATTTGCT    2037

TCCTTTTAGA TGAACGCATT GGTGTCTTTT TTTTCTTCTT TTAAAATAAA TCTCCCTTGC    2097

TGCATTTGAC CAGGAAAAGA AAGCATATAT GCATGTGCAC CGGGCTGTTA TTTTTAAGAT    2157

ATGTAGCTCT ATAAAACGCT ATAGTCAAAA GATGGTAAAA TGTGCAAGAT TCTGGGTGTG    2217

TGTATTAATG TGTGTGTGTC CGCATACACT CACACTCAAG CTGAAGTGAA CGACAGGCCT    2277

GTGCACTGGC CTGCACTTTA TCATTTGGAT TTGTGCTGTT TAATGCTCAG TAAAATATGC    2337

TTAATAAAAG GAAAAAAAAA AAAAAAAAAA AAAAAAA                              2374
```

(2) INFORMATION FOR SEQ ID NO: 2:
    (i) SEQUENCE CHARACTERISTICS:
        (A) LENGTH: 325 amino acids
        (B) TYPE: amino acid
        (C) STRANDEDNESS: single
        (D) TOPOLOGY: linear
    (ii) MOLECULE TYPE: protein
    (v) FRAGMENT TYPE: internal (xi) SEQUENCE DESCRIPTION: SEQ ID NO: 2:

```
Met Val Cys Gly Ser Arg Gly Gly Met Leu Leu Pro Ala Gly Leu
 1               5                  10                  15

Leu Ala Leu Ala Ala Leu Cys Leu Leu Arg Val Pro Gly Ala Arg Ala
            20                  25                  30

Ala Ala Cys Glu Pro Val Arg Ile Pro Leu Cys Lys Ser Leu Pro Trp
        35                  40                  45

Asn Met Thr Lys Met Pro Asn His Leu His His Ser Thr Gln Ala Asn
    50                  55                  60

Ala Ile Leu Ala Ile Glu Gln Phe Glu Gly Leu Leu Gly Thr His Cys
65                  70                  75                  80

Ser Pro Asp Leu Leu Phe Phe Leu Cys Ala Met Tyr Ala Pro Ile Cys
                85                  90                  95

Thr Ile Asp Phe Gln His Glu Pro Ile Lys Pro Cys Lys Ser Val Cys
            100                 105                 110

Glu Arg Ala Arg Gln Gly Cys Glu Pro Ile Leu Ile Lys Tyr Arg His
        115                 120                 125

Ser Trp Pro Glu Ser Leu Ala Cys Glu Glu Leu Pro Val Tyr Asp Arg
    130                 135                 140

Gly Val Cys Ile Ser Pro Glu Ala Ile Val Thr Ala Asp Gly Ala Asp
145                 150                 155                 160
```

```
Phe Pro Met Asp Ser Ser Asn Gly Asn Cys Arg Gly Ala Ser Ser Glu
            165                 170                 175
Arg Cys Lys Cys Lys Pro Val Arg Ala Thr Gln Lys Thr Tyr Phe Arg
            180                 185                 190
Asn Asn Tyr Asn Tyr Val Ile Arg Ala Lys Val Lys Glu Ile Lys Thr
            195                 200                 205
Lys Cys His Asp Val Thr Ala Val Val Glu Val Lys Glu Ile Leu Lys
210                 215                 220
Ala Ser Leu Val Asn Ile Pro Arg Glu Thr Val Asn Leu Tyr Thr Ser
225                 230                 235                 240
Ser Gly Cys Leu Cys Pro Pro Leu Asn Val Asn Glu Glu Tyr Leu Ile
            245                 250                 255
Met Gly Tyr Glu Asp Glu Glu Arg Ser Arg Leu Leu Leu Val Glu Gly
            260                 265                 270
Ser Ile Ala Glu Lys Trp Lys Asp Arg Leu Gly Lys Lys Val Lys Arg
            275                 280                 285
Trp Asp Met Lys Leu Arg His Leu Gly Leu Asn Thr Ser Asp Ser Ser
            290                 295                 300
His Ser Asp Ser Thr Gln Ser Gln Lys Pro Gly Arg Asn Ser Asn Ser
305                 310                 315                 320
Arg Gln Ala Arg Asn
            325

(2) INFORMATION FOR SEQ ID NO: 3:

(i) SEQUENCE CHARACTERISTICS:
        (A) LENGTH: 1484 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 208...1182
        (D) OTHER INFORMATION:

(xi) SEQUENCE DESCRIPTION: SEQ ID NO: 3:

CGGGGCCTGG GCGGSAGGGG CGGTGGCTGG AGCTCGGTAA AGCTCGTGGG ACCCCATTGG    60

GGGAATTTGA TCCAAGGAAG CGGTGATTGC CGGGGGAGGA GAAGCTCCCA GATCCTTGTG   120

TCCACTTGCA GCGGGGGAGG CGGAGACGCG GAGCGGGCCT TTTGGCGTCC ACTGCGCGGC   180

TGCACCCTGC CCCATCCTGC CGGGATC ATG GTC TGC GGC AGC CCG GGA GGG ATG   234
                              Met Val Cys Gly Ser Pro Gly Gly Met
                               1               5

CTG CTG CTG CGG GCC GGG CTG CTT GCC CTG GCT GCT CTC TGC CTG CTC    282
Leu Leu Leu Arg Ala Gly Leu Leu Ala Leu Ala Ala Leu Cys Leu Leu
 10              15                  20                  25

CGG GTG CCC GGG GCT CGG GCT GCA GCC TGT GAG CCC GTC CGC ATC CCC    330
Arg Val Pro Gly Ala Arg Ala Ala Ala Cys Glu Pro Val Arg Ile Pro
            30                  35                  40

CTG TGC AAG TCC CTG CCC TGG AAC ATG ACT AAG ATG CCC AAC CAC CTG    378
Leu Cys Lys Ser Leu Pro Trp Asn Met Thr Lys Met Pro Asn His Leu
            45                  50                  55

CAC CAC AGC ACT CAG GCC AAC GCC ATC CTG GCC ATC GAG CAG TTC GAA    426
His His Ser Thr Gln Ala Asn Ala Ile Leu Ala Ile Glu Gln Phe Glu
            60                  65                  70

GGT CTG CTG GGC ACC CAC TGC AGC CCC GAT CTG CTC TTC TTC CTC TGT    474
Gly Leu Leu Gly Thr His Cys Ser Pro Asp Leu Leu Phe Phe Leu Cys
 75              80                  85
```

```
GCC ATG TAC GCG CCC ATC TGC ACC ATT GAC TTC CAG CAC GAG CCC ATC      522
Ala Met Tyr Ala Pro Ile Cys Thr Ile Asp Phe Gln His Glu Pro Ile
 90              95                 100                 105

AAG CCC TGT AAG TCT GTG TGC GAG CGG GCC CGG CAG GGC TGT GAG CCC      570
Lys Pro Cys Lys Ser Val Cys Glu Arg Ala Arg Gln Gly Cys Glu Pro
                110                 115                 120

ATA CTC ATC AAG TAC CGC CAC TCG TGG CCG GAG AAC CTG GCC TGC GAG      618
Ile Leu Ile Lys Tyr Arg His Ser Trp Pro Glu Asn Leu Ala Cys Glu
            125                 130                 135

GAG CTG CCA GTG TAC GAC AGG GGC GTG TGC ATC TCT CCC GAG GCC ATC      666
Glu Leu Pro Val Tyr Asp Arg Gly Val Cys Ile Ser Pro Glu Ala Ile
        140                 145                 150

GTT ACT GCG GAC GGA GCT GAT TTT CCT ATG GAT TCT AGT AAC GGA AAC      714
Val Thr Ala Asp Gly Ala Asp Phe Pro Met Asp Ser Ser Asn Gly Asn
    155                 160                 165

TGT AGA GGG GCA AGC AGT GAA CGC TGT AAA TGT AAG CCT ATT AGA GCT      762
Cys Arg Gly Ala Ser Ser Glu Arg Cys Lys Cys Lys Pro Ile Arg Ala
170                 175                 180                 185

ACA CAG AAG ACC TAT TTC CGG AAC AAT TAC AAC TAT GTC ATT CGG GCT      810
Thr Gln Lys Thr Tyr Phe Arg Asn Asn Tyr Asn Tyr Val Ile Arg Ala
                190                 195                 200

AAA GTT AAA GAG ATA AAG ACT AAG TGC CAT GAT GTG ACT GCA GTA GTG      858
Lys Val Lys Glu Ile Lys Thr Lys Cys His Asp Val Thr Ala Val Val
            205                 210                 215

GAG GTG AAG GAG ATT CTA AAG TCC TCT CTG GTA AAC ATT CCA CGG GAC      906
Glu Val Lys Glu Ile Leu Lys Ser Ser Leu Val Asn Ile Pro Arg Asp
        220                 225                 230

ACT GTC AAC CTC TAT ACC AGC TCT GGC TGC CTC TGC CCT CCA CTT AAT      954
Thr Val Asn Leu Tyr Thr Ser Ser Gly Cys Leu Cys Pro Pro Leu Asn
    235                 240                 245

GTT AAT GAG GAA TAT ATC ATC ATG GGC TAT GAA GAT GAG GAA CGT TCC     1002
Val Asn Glu Glu Tyr Ile Ile Met Gly Tyr Glu Asp Glu Glu Arg Ser
250                 255                 260                 265

AGA TTA CTC TTG GTG GAA GGC TCT ATA GCT GAG AAG TGG AAG GAT CGA     1050
Arg Leu Leu Leu Val Glu Gly Ser Ile Ala Glu Lys Trp Lys Asp Arg
                270                 275                 280

CTC GGT AAA AAA GTT AAG CGC TGG GAT ATG AAG CTT CGT CAT CTT GGA     1098
Leu Gly Lys Lys Val Lys Arg Trp Asp Met Lys Leu Arg His Leu Gly
            285                 290                 295

CTC AGT AAA AGT GAT TCT AGC AAT AGT GAT TCC ACT CAG AGT CAG AAG     1146
Leu Ser Lys Ser Asp Ser Ser Asn Ser Asp Ser Thr Gln Ser Gln Lys
        300                 305                 310

TCT GGC AGG AAC TCG AAC CCC CGG CAA GCA CGC AAC TAAATCCCGA AATACA   1198
Ser Gly Arg Asn Ser Asn Pro Arg Gln Ala Arg Asn
    315                 320                 325

AAAAGTAACA CAGTGGACTT CCTATTAAGA CTTACTTGCA TTGCTGGACT AGCAAAGGAA  1258

AATTGCACTA TTGCACATCA TATTCTATTG TTTACTATAA AAATCATGTG ATAACTGATT  1318

ATTACTTCTG TTTCTCTTTT GGTTTCTGCT TCTCTCTTCT CTCAACCCCT TTGTAATGGT  1378

TTGGGGGCAG ACTCTTAAGT ATATTGTGAG TTTTCTATTT CACTAATCAT GAGAAAAACT  1438

GTTCTTTTGC AATAATAATA AATTAAACAT GCTGTTAAAA AAAAAA                 1484
```

(2) INFORMATION FOR SEQ ID NO: 4:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 4:

| | | | | | | | | | | | | | | |
|---|---|---|---|---|---|---|---|---|---|---|---|---|---|---|
|Met|Val|Cys|Gly|Ser|Pro|Gly|Gly|Met|Leu|Leu|Leu|Arg|Ala|Gly|Leu|
|1| | | |5| | | | |10| | | | |15| |

| | | | | | | | | | | | | | | |
|---|---|---|---|---|---|---|---|---|---|---|---|---|---|---|
|Leu|Ala|Leu|Ala|Ala|Leu|Cys|Leu|Leu|Arg|Val|Pro|Gly|Ala|Arg|Ala|
| | | | |20| | | | |25| | | | |30| |

| | | | | | | | | | | | | | | |
|---|---|---|---|---|---|---|---|---|---|---|---|---|---|---|
|Ala|Ala|Cys|Glu|Pro|Val|Arg|Ile|Pro|Leu|Cys|Lys|Ser|Leu|Pro|Trp|
| | | |35| | | | |40| | | | |45| | |

| | | | | | | | | | | | | | | |
|---|---|---|---|---|---|---|---|---|---|---|---|---|---|---|
|Asn|Met|Thr|Lys|Met|Pro|Asn|His|Leu|His|His|Ser|Thr|Gln|Ala|Asn|
| |50| | | | |55| | | | |60| | | | |

| | | | | | | | | | | | | | | |
|---|---|---|---|---|---|---|---|---|---|---|---|---|---|---|
|Ala|Ile|Leu|Ala|Ile|Glu|Gln|Phe|Glu|Gly|Leu|Leu|Gly|Thr|His|Cys|
|65| | | | |70| | | | |75| | | | |80|

| | | | | | | | | | | | | | | |
|---|---|---|---|---|---|---|---|---|---|---|---|---|---|---|
|Ser|Pro|Asp|Leu|Leu|Phe|Phe|Leu|Cys|Ala|Met|Tyr|Ala|Pro|Ile|Cys|
| | | | |85| | | | |90| | | | |95| |

| | | | | | | | | | | | | | | |
|---|---|---|---|---|---|---|---|---|---|---|---|---|---|---|
|Thr|Ile|Asp|Phe|Gln|His|Glu|Pro|Ile|Lys|Pro|Cys|Lys|Ser|Val|Cys|
| | | |100| | | | |105| | | | |110| | |

| | | | | | | | | | | | | | | |
|---|---|---|---|---|---|---|---|---|---|---|---|---|---|---|
|Glu|Arg|Ala|Arg|Gln|Gly|Cys|Glu|Pro|Ile|Leu|Ile|Lys|Tyr|Arg|His|
| | |115| | | | |120| | | | |125| | | |

| | | | | | | | | | | | | | | |
|---|---|---|---|---|---|---|---|---|---|---|---|---|---|---|
|Ser|Trp|Pro|Glu|Asn|Leu|Ala|Cys|Glu|Glu|Leu|Pro|Val|Tyr|Asp|Arg|
| |130| | | | |135| | | | |140| | | | |

| | | | | | | | | | | | | | | |
|---|---|---|---|---|---|---|---|---|---|---|---|---|---|---|
|Gly|Val|Cys|Ile|Ser|Pro|Glu|Ala|Ile|Val|Thr|Ala|Asp|Gly|Ala|Asp|
|145| | | | |150| | | | |155| | | | |160|

| | | | | | | | | | | | | | | |
|---|---|---|---|---|---|---|---|---|---|---|---|---|---|---|
|Phe|Pro|Met|Asp|Ser|Ser|Asn|Gly|Asn|Cys|Arg|Gly|Ala|Ser|Ser|Glu|
| | | |165| | | | |170| | | | |175| | |

| | | | | | | | | | | | | | | |
|---|---|---|---|---|---|---|---|---|---|---|---|---|---|---|
|Arg|Cys|Lys|Cys|Lys|Pro|Ile|Arg|Ala|Thr|Gln|Lys|Thr|Tyr|Phe|Arg|
| | | |180| | | | |185| | | | |190| | |

| | | | | | | | | | | | | | | |
|---|---|---|---|---|---|---|---|---|---|---|---|---|---|---|
|Asn|Asn|Tyr|Asn|Tyr|Val|Ile|Arg|Ala|Lys|Val|Lys|Glu|Ile|Lys|Thr|
| | |195| | | | |200| | | | |205| | | |

| | | | | | | | | | | | | | | |
|---|---|---|---|---|---|---|---|---|---|---|---|---|---|---|
|Lys|Cys|His|Asp|Val|Thr|Ala|Val|Val|Glu|Val|Lys|Glu|Ile|Leu|Lys|
| |210| | | | |215| | | | |220| | | | |

| | | | | | | | | | | | | | | |
|---|---|---|---|---|---|---|---|---|---|---|---|---|---|---|
|Ser|Ser|Leu|Val|Asn|Ile|Pro|Arg|Asp|Thr|Val|Asn|Leu|Tyr|Thr|Ser|
|225| | | | |230| | | | |235| | | | |240|

| | | | | | | | | | | | | | | |
|---|---|---|---|---|---|---|---|---|---|---|---|---|---|---|
|Ser|Gly|Cys|Leu|Cys|Pro|Pro|Leu|Asn|Val|Asn|Glu|Glu|Tyr|Ile|Ile|
| | | |245| | | | |250| | | | |255| | |

| | | | | | | | | | | | | | | |
|---|---|---|---|---|---|---|---|---|---|---|---|---|---|---|
|Met|Gly|Tyr|Glu|Asp|Glu|Glu|Arg|Ser|Arg|Leu|Leu|Leu|Val|Glu|Gly|
| | | |260| | | | |265| | | | |270| | |

| | | | | | | | | | | | | | | |
|---|---|---|---|---|---|---|---|---|---|---|---|---|---|---|
|Ser|Ile|Ala|Glu|Lys|Trp|Lys|Asp|Arg|Leu|Gly|Lys|Lys|Val|Lys|Arg|
| | |275| | | | |280| | | | |285| | | |

| | | | | | | | | | | | | | | |
|---|---|---|---|---|---|---|---|---|---|---|---|---|---|---|
|Trp|Asp|Met|Lys|Leu|Arg|His|Leu|Gly|Leu|Ser|Lys|Ser|Asp|Ser|Ser|
| |290| | | | |295| | | | |300| | | | |

| | | | | | | | | | | | | | | |
|---|---|---|---|---|---|---|---|---|---|---|---|---|---|---|
|Asn|Ser|Asp|Ser|Thr|Gln|Ser|Gln|Lys|Ser|Gly|Arg|Asn|Ser|Asn|Pro|
|305| | | | |310| | | | |315| | | | |320|

| | | | |
|---|---|---|---|
|Arg|Gln|Ala|Arg|Asn|
| | | |325| |

(2) INFORMATION FOR SEQ ID NO: 5:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Cys Gln Pro Ile Ser Ile Pro Leu Cys Thr Asp Ile Ala Tyr Asn Gln
 1               5                  10                  15

Thr Ile Met Pro Asn Leu Leu Gly His Thr Asn Gln Glu Asp Ala Gly
            20                  25                  30

Leu Glu Val His Gln Phe Tyr Pro Leu Val Lys Val Gln Cys Ser Ala
        35                  40                  45

Glu Leu Lys Phe Phe Leu Cys Ser Met Tyr Ala Pro Val Cys Thr Val
    50                  55                  60

Leu Glu Gln Ala Leu Pro Pro Cys Arg Ser Leu Cys Glu Arg Ala Gln
65                  70                  75                  80

Gly Cys Glu Ala Leu Met Asn Lys Phe Gly Phe Gln Trp Pro Asp Thr
                85                  90                  95

Leu Lys Cys Glu Lys Phe Pro Val His Gly Arg Gly Glu Leu Cys
            100                 105                 110
```

(2) INFORMATION FOR SEQ ID NO: 6:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Cys Glu Pro Ile Thr Ile Ser Ile Cys Lys Asn Ile Pro Tyr Asn Met
 1               5                  10                  15

Thr Ile Met Pro Asn Leu Ile Gly His Thr Lys Gln Glu Glu Ala Gly
            20                  25                  30

Leu Glu Val His Gln Phe Ala Pro Leu Val Lys Ile Gly Cys Ser Asp
        35                  40                  45

Asp Leu Gln Leu Phe Leu Cys Ser Leu Tyr Val Pro Val Cys Thr Ile
    50                  55                  60

Leu Glu Arg Pro Ile Pro Pro Cys Arg Ser Leu Cys Glu Ser Ala Arg
65                  70                  75                  80

Val Cys Glu Lys Leu Met Lys Thr Tyr Asn Phe Asn Trp Pro Glu Asn
                85                  90                  95

Leu Glu Cys Ser Lys Phe Pro Val His Gly Gly Glu Asp Leu Cys
            100                 105                 110
```

(2) INFORMATION FOR SEQ ID NO: 7:

(i) SEQUENCE CHARACTERISTICS:
        (A) LENGTH: 319 amino acids
        (B) TYPE: amino acid
        (C) STRANDEDNESS: single
        (D) TOPOLOGY: linear (xi) SEQUENCE DESCRIPTION: SEQ ID NO: 7:

```
Met Ser Pro Thr Arg Lys Leu Asp Ser Phe Leu Leu Val Ile Pro
 1               5                  10                  15

Gly Leu Val Leu Leu Leu Leu Pro Asn Ala Tyr Cys Ala Ser Cys Glu
            20                  25                  30

Pro Val Arg Ile Pro Met Cys Lys Ser Met Pro Trp Asn Met Thr Lys
        35                  40                  45

Met Pro Asn His Leu His His Ser Thr Gln Ala Asn Ala Ile Leu Ala
```

-continued

```
            50                  55                  60
Ile Glu Gln Phe Glu Gly Leu Leu Thr Thr Glu Cys Ser Gln Asp Leu
 65                  70                  75                  80

Leu Phe Phe Leu Cys Ala Met Tyr Ala Pro Ile Cys Thr Ile Asp Phe
                 85                  90                  95

Gln His Glu Pro Ile Lys Pro Cys Lys Ser Val Cys Glu Arg Ala Arg
            100                 105                 110

Ala Gly Cys Glu Pro Ile Leu Ile Lys Tyr Arg His Ile Trp Pro Glu
            115                 120                 125

Ser Leu Ala Cys Glu Glu Leu Pro Val Tyr Asp Arg Gly Val Cys Ile
130                 135                 140

Ser Pro Glu Ala Ile Val Thr Val Glu Gln Gly Thr Asp Ser Met Pro
145                 150                 155                 160

Asp Phe Pro Met Asp Ser Asn Asn Gly Asn Cys Gly Ser Thr Ala Gly
                165                 170                 175

Glu His Cys Lys Cys Lys Pro Met Lys Ala Ser Gln Lys Thr Tyr Leu
            180                 185                 190

Lys Asn Asn Tyr Asn Tyr Val Ile Arg Ala Lys Val Lys Glu Val Lys
            195                 200                 205

Val Lys Cys His Asp Ala Thr Ala Ile Val Glu Val Lys Glu Ile Leu
210                 215                 220

Lys Ser Ser Leu Val Asn Ile Pro Lys Asp Thr Val Ile Leu Tyr Thr
225                 230                 235                 240

Asn Ser Gly Cys Leu Cys Pro Gln Leu Val Ala Asn Glu Glu Tyr Ile
                245                 250                 255

Ile Met Gly Tyr Glu Asp Lys Glu Arg Thr Arg Leu Leu Val Glu
                260                 265                 270

Gly Ser Leu Ala Glu Lys Trp Arg Asp Arg Leu Ala Lys Lys Val Lys
            275                 280                 285

Arg Trp Asp Gln Lys Leu Arg Arg Pro Arg Lys Ser Lys Asp Pro Val
            290                 295                 300

Ala Pro Ile Pro Asn Lys Asn Ser Asn Ser Arg Gln Ala Arg Ser
305                 310                 315

(2) INFORMATION FOR SEQ ID NO: 8:

(i) SEQUENCE CHARACTERISTICS:
        (A) LENGTH: 318 amino acids
        (B) TYPE: amino acid
        (C) STRANDEDNESS: single
        (D) TOPOLOGY: linear (xi) SEQUENCE DESCRIPTION: SEQ ID NO: 8:

Met Val Cys Gly Ser Gly Gly Met Leu Leu Leu Ala Gly Leu Leu Ala
 1               5                  10                  15

Leu Ala Ala Leu Leu Leu Arg Val Pro Gly Ala Arg Ala Ala Ala Cys
                 20                  25                  30

Glu Pro Val Arg Ile Pro Leu Cys Lys Ser Leu Pro Trp Asn Met Thr
             35                  40                  45

Lys Met Pro Asn His Leu His His Ser Thr Gln Ala Asn Ala Ile Leu
 50                  55                  60

Ala Ile Glu Gln Phe Glu Gly Leu Leu Gly Thr His Cys Ser Pro Asp
 65                  70                  75                  80

Leu Leu Phe Phe Leu Cys Ala Met Tyr Ala Pro Ile Cys Thr Ile Asp
                 85                  90                  95
```

```
Phe Gln His Glu Pro Ile Lys Pro Cys Lys Ser Val Cys Glu Arg Ala
            100                 105                 110

Arg Gln Gly Cys Glu Pro Ile Leu Ile Lys Tyr Arg His Ser Trp Pro
            115                 120                 125

Glu Ser Leu Ala Cys Glu Leu Pro Val Tyr Asp Arg Gly Val Cys
            130                 135                 140

Ile Ser Pro Glu Ala Ile Val Thr Ala Asp Gly Ala Asp Phe Pro Met
145                 150                 155                 160

Asp Ser Ser Asn Gly Asn Cys Arg Gly Ala Ser Ser Glu Arg Cys Lys
                165                 170                 175

Cys Lys Pro Arg Ala Ile Gln Lys Thr Tyr Phe Arg Asn Asn Tyr Asn
                180                 185                 190

Tyr Val Ile Arg Ala Lys Val Lys Glu Ile Lys Ile Lys Cys His Asp
                195                 200                 205

Val Thr Ala Val Val Glu Val Lys Glu Ile Leu Lys Ser Ser Leu Val
        210                 215                 220

Asn Ile Pro Arg Asp Thr Val Asn Leu Tyr Thr Ser Ser Gly Cys Leu
225                 230                 235                 240

Cys Pro Pro Leu Asn Val Asn Glu Glu Tyr Ile Ile Met Gly Tyr Glu
                245                 250                 255

Asp Glu Glu Arg Ser Arg Leu Leu Val Glu Gly Ser Ile Ala Glu
            260                 265                 270

Lys Trp Lys Asp Arg Leu Gly Lys Val Lys Arg Trp Asp Met Lys
            275                 280                 285

Leu Arg His Leu Gly Leu Ser Asp Ser Ser Asp Ser Thr Gln Ser
            290                 295                 300

Gln Lys Pro Gly Arg Asn Ser Asn Ser Arg Gln Ala Arg Asn
305                 310                 315
```

(2) INFORMATION FOR SEQ ID NO: 9:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

```
Glu Thr Val Asn Leu Tyr Thr Ser Ala Gly Cys Leu Cys Pro Pro Leu
1               5                   10                  15

Asn Val Asn Glu Glu Tyr Leu Ile Met Gly Tyr Glu Phe Pro
            20                  25                  30
```

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GARACHGTSA AYCTBTAYAC N                                          21

(2) INFORMATION FOR SEQ ID NO: 11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 11:

RAAYTCRTAN CCCATNAT                                                     18

(2) INFORMATION FOR SEQ ID NO: 12:

(i) SEQUENCE CHARACTERISTICS:
            (A) LENGTH: 19 amino acids
            (B) TYPE: amino acid
            (C) STRANDEDNESS: single
            (D) TOPOLOGY: linear (ix) FEATURE:
            (A) NAME/KEY: Other
            (B) LOCATION: 13...13
            (D) OTHER INFORMATION: Aspartic Acid or Histidine (xi) SEQUENCE DESCRIPTION: SEQ ID NO: 12:

Gly Val Cys Ile Ser Pro Glu Ala Ile Val Thr Ala Xaa Gly Ala Asp
1               5                  10                  15

Phe Pro Met (2) INFORMATION FOR SEQ ID NO: 13:

(i) SEQUENCE CHARACTERISTICS:
            (A) LENGTH: 9 amino acids
            (B) TYPE: amino acid
            (C) STRANDEDNESS: single
            (D) TOPOLOGY: linear (xi) SEQUENCE DESCRIPTION: SEQ ID NO: 13:

Gln Gly Cys Glu Pro Ile Leu Ile Lys
1               5

(2) INFORMATION FOR SEQ ID NO: 14:

(i) SEQUENCE CHARACTERISTICS:
            (A) LENGTH: 15 amino acids
            (B) TYPE: amino acid
            (C) STRANDEDNESS: single
            (D) TOPOLOGY: linear (xi) SEQUENCE DESCRIPTION: SEQ ID NO: 14:

Gln Gly Cys Glu Pro Ile Leu Ile Cys Ala Trp Pro Pro Leu Tyr
1               5                  10                  15

(2) INFORMATION FOR SEQ ID NO: 15:

(i) SEQUENCE CHARACTERISTICS:
            (A) LENGTH: 28 amino acids
            (B) TYPE: amino acid
            (C) STRANDEDNESS: single
            (D) TOPOLOGY: linear (xi) SEQUENCE DESCRIPTION: SEQ ID NO: 15:

Glu Thr Val Asn Leu Tyr Thr Ser Ala Gly Cys Leu Cys Pro Pro Leu
1               5                  10                  15

Asn Val Asn Glu Glu Tyr Leu Ile Met Gly Tyr Glu
            20                  25

(2) INFORMATION FOR SEQ ID NO: 16:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 16:

```
Glu Thr Val Asn Leu Tyr Thr Ser Ser Gly Cys Leu Cys Pro Pro Leu
 1               5                  10                  15

Asn Val Asn Glu Glu Tyr Leu Ile Met Gly Tyr Glu
             20                  25
```

(2) INFORMATION FOR SEQ ID NO: 17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

GCTCTGGCTG CCTGTGTCCT CCACTTAACG                    30

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 18:

CCTCCACTTA ACGTTAATGA GGAGTATCTC                    30

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 19:

TGGAACATGA CTAAGATGCC C                               21

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 20:

CATATACTGG CAGCTCCTCG                              20

(2) INFORMATION FOR SEQ ID NO: 21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 21:

GTCTTTTGGG AAGCCTTCAT GG        22

(2) INFORMATION FOR SEQ ID NO: 22:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (xi) SEQUENCE DESCRIPTION: SEQ ID NO: 22:

GCATCGTGGC ATTTCACTTT CA        22

(2) INFORMATION FOR SEQ ID NO: 23:

(i) SEQUENCE CHARACTERISTICS:
      (A) LENGTH: 1291 base pairs
      (B) TYPE: nucleic acid
      (C) STRANDEDNESS: single
      (D) TOPOLOGY: linear (xi) SEQUENCE DESCRIPTION: SEQ ID NO: 23:

```
TTTACTGTGC CAGTCTTCCC TGTAACCAGC GACCTGTATT CCCCCAAGTA AGCCTACACA        60
TACAGGTTGG GCAGAATAAC AATGTCTCCA ACAAGGAAAT TGGACTCATT CCTGCTACTG       120
GTCATACCTG GACTGGTGCT TCTCTTATTA CCCAATGCTT ACTGTGCTTC GTGTGAGCCT       180
GTGCGGATTC CCATGTGCAA ATCTATGCCA TGGAACATGA CCAAGATGCC CAACCATCTC       240
CACCACAGCA CTCAAGCCAA TGCTATCCTG GCAATTGAAC AGTTTGAAGG TTTGCTGACC       300
ACTGAATGTA GCCAGGACCT TTTGTTCTTT CTGTGTGCCA TGTATGCCCC CATTTGTACC       360
ATCGATTTCC AGCATGAACC AATTAAGCCT TGCAAGTCCG TGTGCGAAAG GGCCAGGGCC       420
GGCTGTGAGC CCATTCTCAT AAAGTACCGG CACACTTGGC CAGAGAGCCT GGCATGTGAA       480
GAGCTGCCCG TATATGACAG AGGAGTCTGC ATCTCCCCAG AGGCTATCGT CACAGTGGAA       540
CAAGGAACAG ATTCAATGCC AGACTTCCCC ATGGATTCAA ACAATGGAAA TTGCGGAAGC       600
ACGGCAGGTG AGCACTGTAA ATGCAAGCCC ATGAAGGCTT CCCAAAAGAC GTATCTCAAG       660
AATAATTACA ATTATGTAAT CAGAGCAAAA GTGAAAGAGG TGAAAGTGAA ATGCCACGAC       720
GCAACAGCAA TTGTGGAAGT AAAGGAGATT CTCAAGTCTT CCCTAGTGAA CATTCCTAAA       780
GACACAGTGA CACTGTACAC CAACTCAGGC TGCTTGTGCC CCAGCTTGT TGCCAATGAG        840
GAATACATAA TTATGGGCTA TGAAGACAAA GAGCGTACCA GGCTTCTACT AGTGGAAGGA       900
TCCTTGGCCG AAAAATGGAG AGATCGTCTT GCTAAGAAAG TCAAGCGCTG GGATCAAAAG       960
CTTCGACGTC CCAGGAAAAG CAAAGACCCC GTGGCTCCAA TTCCCAACAA AAACAGCAAT      1020
TCCAGACAAG CGCGTAGTTA GACTAACGGA AAGGTGTATG GAAACTCTAT GGACTTTGAA      1080
ACTAAGATTT GCATTGTTGG AAGAGCAAAA AAGAAATTGC ACTACAGCAC GTTATATTCT      1140
ATTGTTTACT ACAAGAAGCT GGTTTAGTTG ATTGTAGTTC TCCTTTCCTT CTTTTTTTTA      1200
TAACTATATT GCACGTGTTC CAGGCAGTTT ATCAACTTCC AGTGACAGAG CAGTGACTGA      1260
ATGTAGCTAA GAGCCTATCA TCTGATCACT A                                    1291
```